(12) United States Patent
Vilfan et al.

(10) Patent No.: US 9,879,318 B2
(45) Date of Patent: Jan. 30, 2018

(54) METHODS AND COMPOSITIONS FOR NUCLEIC ACID SAMPLE PREPARATION

(71) Applicant: Pacific Biosciences of California, Inc., Menlo Park, CA (US)

(72) Inventors: Igor Vilfan, East Palo Alto, CA (US); Stephen Turner, Seattle, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 431 days.

(21) Appl. No.: 14/477,472

(22) Filed: Sep. 4, 2014

(65) Prior Publication Data

US 2015/0072869 A1  Mar. 12, 2015

Related U.S. Application Data

(60) Provisional application No. 61/874,464, filed on Sep. 6, 2013.

(51) Int. Cl.
*C12Q 1/68* (2006.01)
*C12N 15/10* (2006.01)

(52) U.S. Cl.
CPC ....... *C12Q 1/6869* (2013.01); *C12N 15/1096* (2013.01); *C12Q 1/6844* (2013.01); *C12Q 2535/122* (2013.01)

(58) Field of Classification Search
None
See application file for complete search history.

(56) References Cited

U.S. PATENT DOCUMENTS

| | | | |
|---|---|---|---|
| 6,083,482 A * | 7/2000 | Wang | C07H 19/04 424/1.73 |
| 6,917,726 B2 | 7/2005 | Levene et al. | |
| 7,056,661 B2 | 6/2006 | Korlach et al. | |
| 7,315,019 B2 | 1/2008 | Turner et al. | |
| 8,003,330 B2 | 8/2011 | Heiner et al. | |
| 8,153,375 B2 | 4/2012 | Travers et al. | |
| 8,182,993 B2 | 5/2012 | Tomaney et al. | |
| 8,309,330 B2 | 11/2012 | Travers et al. | |
| 8,370,079 B2 | 2/2013 | Sorenson et al. | |
| 8,501,405 B2 | 8/2013 | Korlach et al. | |
| 8,628,940 B2 | 1/2014 | Sorenson et al. | |
| 2010/0081143 A1 | 4/2010 | Rank et al. | |
| 2011/0183320 A1 | 7/2011 | Flusberg et al. | |
| 2012/0196279 A1 | 8/2012 | Underwood et al. | |
| 2012/0330566 A1 | 12/2012 | Chaisson | |
| 2013/0138358 A1 | 5/2013 | Tang et al. | |

OTHER PUBLICATIONS

Makeyev, EV. et al. Primer-independent RNA sequencing with bacteriophase Phi6 RNA polymerase and chain terminators. RNA, vol. 7, p. 774-781, 2001.*
Artsimovitch et al. Interaction of a nascent RNA structure with RNA polymerase is required for hairpin-dependent transcriptional pausing but not for transcript release. Genes and Development, vol. 12, p. 3110-3122, 1998.*
Chan et al., "Advances in Sequencing Technology," Mutation Research (2005) 573:13-40.
Eid et al., "Real-Time DNA Sequencing From Single Polymerase Molecules," Science (2009) 323:133-138.
Korlach et al., "Long, Processive Enzymatic DNA Synthesis Using 100% Dye-Labeled Terminal Phosphate-Linked Nucleotides." Nucleosides, Nucleotides and Nucleic Acids (2008) 27:1072-1083.
Korlach et al., "Real-Time DNA Sequencing From Single Polymerase Molecules," Methods in Enzymology (2010) 472:431-455.
Majlessi et al., "Advantages of 2'-O-methyl Oligoribonucleotide Probes for Detecting RNA Targets," Nucl. Acids Res. (1998) 26(9):2224-2229.
Makeyev et al., "Primer-Independent RNA Sequencing with Bacteriophage φ6 RNA Polymerase and Chain Terminators," RNA (2001) 7:774-781.
Nielsen et al., "Sequence-selective recognition of DNA by strand displacement with a thymin-substituted polyamide," Science (1991) 254(5038):1497-1500.
Stump et al., "The Use of Modified Primers to Eliminate Cycle Sequencing Artifacts," Nucl. Acids Res. (1999) 27 (23):4642-4648.
Travers et al., "A Flexible and Efficient Template Format for Circular Consensus Sequencing and SNP Detection," Nucl. Acids. Res (2010) 38(15):e159.

* cited by examiner

Primary Examiner — Suryaprabha Chunduru
(74) Attorney, Agent, or Firm — David C. Scherer

(57) ABSTRACT

The present invention provides methods and compositions useful for supplying high throughput nucleic acid sequencing systems with templates. The methods circumvent the need for costly, labor-intensive cloning and cell culture methods and can be scaled to accommodate template production for a variety of sequencing applications, e.g., sequencing individuals' genomes, sequencing subpopulations of transcripts from a gene of interest, and/or gene expression profiling. Particularly preferred embodiments of the methods vastly improve the preparation of cDNA from mRNA samples, e.g., by randomizing errors introduced during the process, thereby allowing these errors to be readily distinguished from true variants present in the mRNA samples.

27 Claims, 8 Drawing Sheets

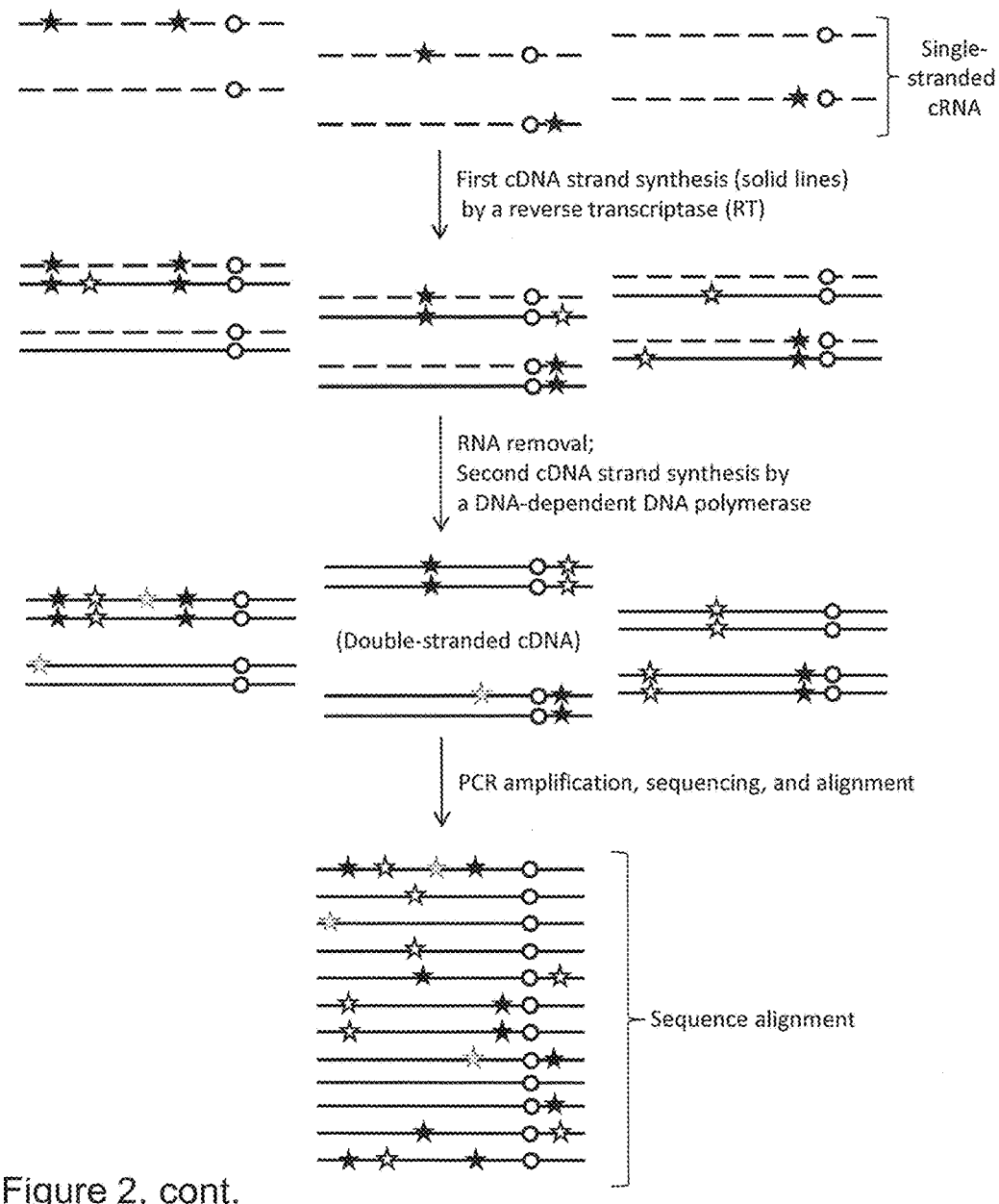
Figure 2, cont.

A. Adaptor:

B. Invading oligo:

A.

B.

Lane 1: dsDNA laddder
Lane 2: RT-PCR of amplified RNA with both PCR primer present in RT step
Lane 3: RT-PCR of amplified RNA with second-strand primer present in RT step
Lane 4: RT-PCR of amplified RNA with first-strand primer present in RT step Lane 1: 1.8 kb mRNA + 6 minute extension time; no Phi6 replicase (neg. control)
Lane 2: 1.8 kb mRNA + 6 minute extension time + Phi6 replicase
Lane 3: 1.8 kb mRNA + 22 minute extension time; no Phi6 replicase (neg. control)
Lane 4: 1.8 kb mRNA + 22 minute extension time + Phi6 replicase

SEQUENCE LISTING

<160> NUMBER OF SEQ ID NOS: 3

<210> SEQ ID NO 1
<211> LENGTH: 20
<212> TYPE: RNA
<213> ORGANISM: Artificial Sequence
<220> FEATURE:
<223> OTHER INFORMATION: adaptor sequence
<220> FEATURE:
<221> NAME/KEY: misc_feature
<222> LOCATION: (2)..(11)
<223> OTHER INFORMATION: n is a, c, g, or u
<220> FEATURE:
<221> NAME/KEY: misc_structure
<222> LOCATION: (20)..(20)
<223> OTHER INFORMATION: dideoxycytidine

<400> SEQUENCE: 1
annnnnnnnn nuuuuuuucc                                              20

<210> SEQ ID NO 2
<211> LENGTH: 11
<212> TYPE: DNA
<213> ORGANISM: Artificial Sequence

```
<220> FEATURE:
<223> OTHER INFORMATION: invading oligonucleotide
<220> FEATURE:
<221> NAME/KEY: misc_structure
<222> LOCATION: (1)..(11)
<223> OTHER INFORMATION: locked nucleic acid

<400> SEQUENCE: 2
tttttttcct t                                                                11

<210> SEQ ID NO 3
<211> LENGTH: 10
<212> TYPE: RNA
<213> ORGANISM: Artificial Sequence
<220> FEATURE:
<223> OTHER INFORMATION: initiation sequence

<400> SEQUENCE: 3
uuuuuuuucc                                                                  10
```

METHODS AND COMPOSITIONS FOR NUCLEIC ACID SAMPLE PREPARATION

CROSS-REFERENCE TO RELATED APPLICATIONS

This application claims the benefit of U.S. Provisional Application No. 61/874,464, filed Sep. 6, 2013, the disclosure of which is incorporated herein by reference in its entirety for all purposes.

STATEMENT REGARDING FEDERALLY SPONSORED RESEARCH

This invention was made with government support under Grant No. R01HG003710 awarded by the National Human Genome Research Institute (NHGRI) of the National Institutes of Health (NIH). The government has certain rights in the invention. The preceding statement is included in accordance with 37 C.F.R. 401.14(f)(4) because one or more inventions described herein were made or developed with government grant support. This statement should not be construed as necessarily covering all inventions described herein.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only a 2 KB file (01015301_2014-10-15_SequenceListing.txt).

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs and improve accuracy (See, e.g., Chan, et al. (2005) "Advances in Sequencing Technology" (Review) Mutation Research 573: 13-40, Levene et al. (2003) "Zero Mode Waveguides for Single Molecule Analysis at High Concentrations," Science 299: 682-686).

Current methods for preparing nucleic acid templates are not optimal for use in high throughput DNA sequencing systems, especially those that determine nucleotide sequences from single molecules of a template. Conventional cloning and cell culture methods are time consuming and expensive. Lengthy nucleic acid purification protocols currently in use do not reliably produce nucleic acid samples that are sufficiently free of sequencing reaction inhibitors such as salts, carbohydrates and/or proteins. Methods that utilize amplification introduce errors into the resulting amplicons that can be difficult to distinguish from true variants in the original sample. Furthermore, these problems are magnified when such conventional techniques are scaled to the quantities that would be useful for high throughput sequencing technologies. Consequently, there is an increasing demand for efficient, low-cost methods for the preparation of high-quality nucleic acid templates. In particular, such templates should either be error-free, or be amplified in such a way that any errors introduced during the amplification (or other steps of the template preparation) are distinguishable from genetic variants originally present in the sample nucleic acid. The present invention provides methods and compositions that would be useful for supplying high throughput DNA sequencing systems with such templates.

SUMMARY OF CERTAIN ASPECTS OF THE INVENTION

The present invention provides methods and compositions that can be useful for supplying high throughput nucleic acid sequencing systems with templates. The methods circumvent the need for costly, labor-intensive cloning and cell culture methods and can be scaled to accommodate template production for a variety of sequencing applications, e.g., sequencing individuals' genomes, sequencing subpopulations of transcripts from a gene of interest, and/or gene expression profiling (Spinella, et al. (1999) "Tandem arrayed ligation of expressed sequence tags (TALEST): a new method for generating global gene expression profiles." Nucleic Acids Res 27: e22, Velculescu, et al. (1995) "Serial analysis of gene expression." Science 270: 484-487). The methods and compositions provided by the invention can be used to produce either linear or circular single-stranded nucleic acid templates. In particularly preferred embodiments, certain of the methods vastly improve the preparation of cDNA from mRNA samples, e.g., by randomizing errors introduced during the process, thereby allowing these errors to be readily distinguished from true variants present in the mRNA samples.

In certain aspects, the invention provides methods of performing linear amplification of a plurality of sample RNA molecules. Preferred embodiments comprise providing a plurality of sample RNA molecules, wherein the plurality of sample RNA molecules have differing nucleotide compositions; linking an adaptor to all 3' ends of said plurality of sample RNA molecules, wherein the adaptor comprises a barcode region and a Phi6 RNA replicase initiation sequence in a common region, and further wherein each adaptor has a different barcode region; synthesizing a complementary nascent RNA strand for each of the sample RNA molecules by replicating the sample RNA molecules with Phi6 RNA replicase, thereby generating double-stranded RNA molecules; providing an oligonucleotide complementary to a segment of the first nascent RNA strand, wherein the segment is complementary to at least a portion of the common region of the adaptor; annealing the oligonucleotide to the first nascent RNA strand, thereby separating a 5' end of the first nascent RNA strand from the 3' end of the sample RNA molecule; repeating said synthesis, whereby the first nascent RNA strand is strand-displaced and a second nascent RNA strand is synthesized; and repeating said annealing and said synthesis multiple times, thereby performing linear amplification of the plurality of RNA molecules and producing a pool of amplified RNA molecules. In some embodiments, the annealing and synthesizing is repeated 5, 10, 15, 20, 25, 30, 35, 40, 45, or 50 times. Preferably, the oligonucleotide is at least partly an LNA, or locked nucleic acid. In preferred embodiments, the oligonucleotide is 5'-adenylated, e.g., to enhance ligation to a sample RNA molecule. In contrast, the adaptor is typically dideoxy-terminated on the 3' end. The barcode region optionally comprises randomized bases, preferably such that each barcode in the mixture comprises a different base sequence. In certain embodiments, the pool of amplified RNA molecules is converted to double-stranded cDNA, which can be optionally amplified prior to further analysis. Nucleotide sequences can be determined for the pool of amplified RNA molecules, and these nucleotide sequences comprise sequences from the nucleic acids of the sample RNA ("sample RNA sequences") and sequences from the barcode regions ("barcode sequences"). These barcode sequences serve as a tag that links the sequences of the nascent RNAs back to the original sample RNA molecules, since all nucleic acids that descended from a single adaptor-linked sample RNA molecule will have the same barcode sequence.

The synthesis and strand-displacement/annealing can be carried out at the same temperature, or the reaction can be cycled between two temperatures, one more optimal for the synthesis and one more optimal for the strand-displacement/annealing. For example, both can be performed at the temperature more optimal for the annealing, where the enzyme will function sufficiently at that temperature. In a specific embodiment using the Phi6 RNA replicase, both reactions can be performed at 40° C., or the reaction mixture can be cycled between 32° C. (optimal for Phi6) and 40° C. (optimal for strand-displacement/annealing).

In other aspects, the invention provides methods for cDNA conversion of an RNA molecule. Certain such embodiments comprise: providing an RNA molecule; linking an adaptor comprising a Phi6 RNA replicase initiation sequence, and preferably also a barcode sequence, to a 3' end of said RNA molecule; synthesizing a first nascent RNA strand that is complementary to the RNA molecule by contacting said RNA molecule with Phi6 RNA replicase, thereby generating a double-stranded RNA molecule; providing an oligonucleotide complementary to a segment of the first nascent RNA strand, wherein the segment is complementary to at least a portion of the adaptor; annealing the oligonucleotide to the first nascent RNA strand, thereby separating a 5' end of the first nascent RNA strand from the 3' end of said RNA molecule; repeating said synthesis, whereby the first nascent RNA strand is displaced and a second nascent RNA strand is synthesized; repeating said annealing and said synthesis multiple times, thereby performing linear amplification of the RNA molecule and producing multiple nascent RNA strands complementary to the RNA molecule; and converting the multiple nascent RNA strands complementary to the RNA molecule into cDNAs, thereby generating a pool of cDNAs in which errors introduced during repeated synthesis, as well as cDNA synthesis and amplification, are randomly distributed. In some embodiments, the strand-displacement/annealing and synthesis is repeated 5, 10, 15, 20, 25, 30, 35, 40, 45, or 50 times. Preferably, the oligonucleotide is at least partly an LNA, or locked nucleic acid. In preferred embodiments, the oligonucleotide is 5'-adenylated. In contrast, the adaptor is typically dideoxy-terminated on the 3' end. In certain preferred embodiments, the adaptor also comprises a barcode, e.g., comprising randomized bases. Where sequencing is performed, barcode sequences can be used to identify a set of sequence reads that all correspond to (e.g., originated from) the same original RNA molecule. This is especially useful in multiplex analysis when multiple variants of the same RNA sequence are present in a sample. The molecules do not have to be separately analyzed because the barcodes allow all the "descendent" sequences from a single RNA molecule to be analyzed together to provide, e.g., a consensus sequence for that single RNA molecule.

The pool of cDNAs can be subsequently subjected to additional analysis or manipulations, e.g., sequencing, cloning, amplification, etc. In some embodiments, amplification of the pool of cDNAs generates a pool of cDNA amplicons, and errors introduced during repetitions of the synthesizing are randomly distributed in the cDNA amplicons, at least because the errors were introduced randomly and, thus, a cDNA in the resulting pool that does have an error is unlikely to have the same error as another cDNA in the pool. This amplification can occur separate from the cDNA conversion, or cDNA conversion and amplification can occur in the same reaction mixture.

In other aspects, methods are provided for performing multiplex analysis of retroviral populations. In preferred embodiments, such methods comprise: providing linear genetic material from a retroviral population, wherein the genomic material comprises multiple viral genomes, each having a different set of sequence variants; linking an adaptor to all 3' ends of said linear genetic material, wherein the adaptor comprises a barcode region and a Phi6 RNA replicase initiation sequence in a common region, and further wherein each adaptor has a different barcode region, thereby generating adaptor-linked viral RNAs; synthesizing first nascent RNA strands for each of the adaptor-linked viral RNAs, wherein the first nascent RNA strand are complementary to the adaptor-linked viral RNAs, wherein the synthesizing comprises contacting said adaptor-linked viral RNAs with Phi6 RNA replicase, thereby generating double-stranded RNA molecules; providing oligonucleotides complementary to segments of the first nascent RNA strands, wherein the segments are complementary to at least a portion of the adaptor; annealing the oligonucleotides to the first nascent RNA strands, thereby separating 5' ends of the first nascent RNA strands from 3' ends of the adaptor-linked viral RNAs; repeating said synthesizing, whereby the first nascent RNA strands are displaced and second nascent RNA strands are synthesized; repeating said annealing and said synthesizing multiple times, thereby performing linear amplification of the adaptor-linked viral RNAs and producing multiple nascent RNA strands complementary to each of the adaptor-linked viral RNAs; converting the multiple nascent RNA strands complementary to the adaptor-linked viral RNAs into cDNAs, thereby generating a pool of cDNAs in which all members of the pool of cDNAs that are descended from one of the adaptor-linked viral RNAs comprise identical barcode regions; determining nucleotide sequences for the member of the pool of cDNAs, wherein the nucleotide sequences comprise adaptor-linked viral RNA sequences and barcode sequences; grouping the nucleotide sequences based on the barcode sequences, wherein all nucleotide sequences from members of the pool of cDNAs that are descended from one of the adaptor-linked viral RNAs are grouped together, thereby composing one group of the nucleotide sequences for each of the adaptor-linked viral RNAs; and using the adaptor-linked viral RNA sequences in each group composed to construct a consensus sequence for each of the adaptor-linked viral RNAs. In some embodiments, the linear genomic material comprises fragmented viral genomes, and in other embodiments, the linear genomic material comprises full-length viral genomes. Optionally, the pool of cDNAs can be amplified prior to determining the nucleotide sequences. Synthesizing nucleic acids, whether the nascent RNA strands or during the conversion to cDNA, is imperfect and typically some of the nascent RNA strands will comprise errors. The methods herein randomize these errors so they can easily be corrected during data analysis. While the "true" variants present in the original RNA will be present in essentially all of the amplified RNAs and subsequent cDNAs synthesized and amplified, the an error introduced during the nucleic acid synthesis steps will be present in only a minority of the RNAs and cDNAs. As such, the consensus sequences constructed from sequence reads of these cDNAs will contain the true variants, but not the errors, which will be discarded during consensus sequence determination.

DETAILED DESCRIPTION

Figure 1:
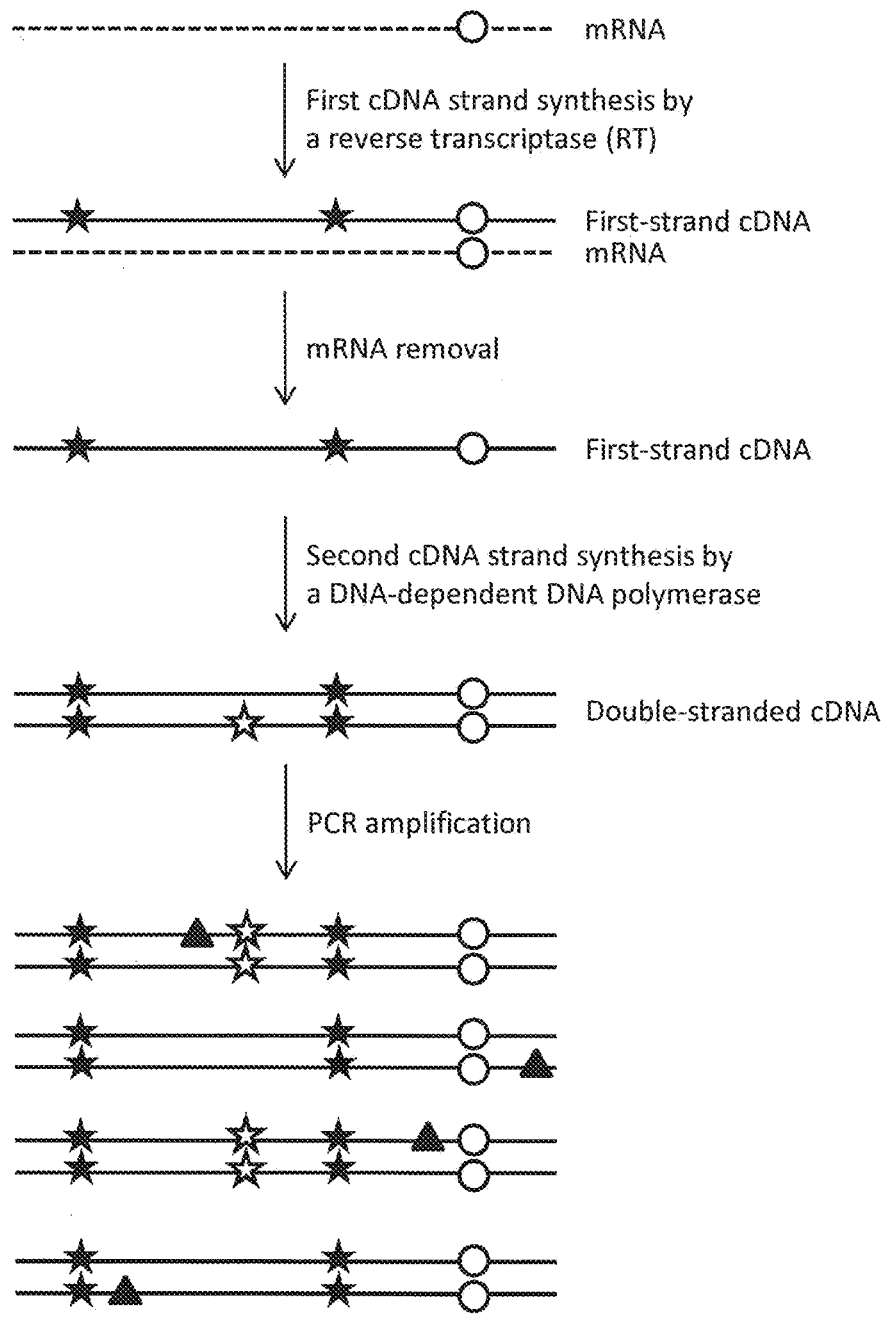
FIG. 1 provides an illustrative example of how traditional cDNA synthesis results in propagation of errors in the resulting cDNA molecules.

Collecting reliable sequence data using high-throughput sequencing technologies depends in part on the availability of methods for the rapid and efficient production of high-quality nucleic acid templates. Further, it is also important that any changes in the sequences of the templates that are introduced during their production be distinguishable from sequence variants that were present in the original nucleic acid samples. The present invention provides methods and compositions that can be useful in supplying templates to such high throughput DNA sequencing systems. The methods circumvent the need for costly, labor-intensive cloning and cell culture methods, which can limit sample production, e.g., preventing it from matching the capacities of modern sequencing systems (such systems are described in, e.g., Chan, et al. (2005) "Advances in Sequencing Technology" *Mutation Research* 573: 13-40; Levene et al. (2003) "Zero Mode Waveguides for Single Molecule Analysis at High Concentrations," *Science* 299: 682-686; Korlach, et al. (2008) "Long, Processive Enzymatic DNA Synthesis Using 100% Dye-Labeled Terminal Phosphate-Linked Nucleotides" *Nucleotides, Nucleosides, and Nucleic Acids* 27:1072-1083; Travers, et al. (2010) "A flexible and efficient template format for circular consensus sequencing and SNP detection" *Nucl. Acids Res.* 38(15):e159; Korlach, et al. (2010) "Real-time DNA sequencing from single polymerase molecules" *Methods in Enzymology* 472:431-455; and Eid et al. (2009) Science 323:133-138, the disclosures of which are incorporated herein by reference in their entireties for all purposes). In certain preferred embodiments, the methods provide template preparation methods whereby base misincorporations, deletions, and/or insertions introduced during the template preparation process are randomized to facilitate discrimination from true variants present in the original sample nucleic acid molecules. For example, variants present in an mRNA molecule are maintained and can be identified in the resulting cDNA template, but any misincorporation events that occurred during the linear amplification of the mRNA molecule, the cDNA preparation, e.g., during first- and second-strand synthesis, and/or subsequent amplification of the cDNA, are randomly distributed in the resulting pool of template cDNA molecules. As such, these "introduced" variants can be readily distinguished from the "true" variants using sequencing data generated from the cDNA templates, as further described below. Accordingly, a reduction in sequencing costs is an expected benefit of the improved methods described herein, at least because a lower-fold sequencing of a pool of templates with random misincorporation errors can achieve the same high consensus, and maybe higher, than a higher-fold sequencing of templates comprising misincorporation and other errors that have been propagated by synthesis and/or amplification of the template prior to sequencing and that cannot be distinguished from true variants present in the original mRNA molecule. The methods can be scaled to accommodate template production for a variety of sequencing applications, but are particularly useful for preparation of cDNAs and amplification of RNAs and cDNAs, e.g., for use as templates in nucleic acid sequencing reactions.

The nucleic acids to be sequenced can be obtained from any source of interest, and can comprise DNA, RNA (e.g., mRNA), and mimetics, analogs, and derivatives thereof. They can be isolated from cells, cell cultures, tissue samples, bodily fluids, viral samples, genomic nucleic acid samples, cDNA preparations, environmental samples, forensic samples, or synthetic sources. Nucleic acids can be cloned, amplified, transcribed, ligated, fragmented, or otherwise manipulated according to standard methods to provide the nucleic acid to be further manipulated and/or sequenced as these manipulations do not render the nucleic acid unsuitable for subsequent sequencing as described herein. It will be understood that such nucleic acids may comprise modified, non-canonical, and/or non-natural nucleotides or nucleotide analogs, many of which are described in U.S. patent application Ser. No. 12/945,767, filed Nov. 12, 2010, which is incorporated herein by reference in its entirety for all purposes. In particularly preferred embodiments, nucleic acids isolated from a source are mRNA molecules, e.g., full-length mRNA molecules, and these mRNA molecules are used to prepare a cDNA library. In other particularly preferred embodiments, nucleic acids isolated from a source are DNA molecules, which are subsequently transcribed into mRNA molecules used to prepare a cDNA library. In yet further particularly preferred embodiments, nucleic acids isolated from a source are viral RNA molecules, e.g., viral RNA genomes from an organism in which a virus is replicating and, potentially, mutating. Yet further, although various methods are described that use mRNA as a starting nucleic acid, it will be understood that other forms of RNA are contemplated in these methods, as well, e.g., rRNA, tRNA, genomic RNA (e.g., retroviral genomes), ribozyme RNA (e.g., ribonuclease P, ribonuclease MRP, etc.), SRP RNA, tmRNA, snRNA, snoRNA, SmY RNA, gRNA, scaRNA, Y RNA, vRNA, telomerase RNA, spliced leader RNA, regulatory RNA (e.g., antisense RNA, CRISPR RNA, long ncRNA, miRNA, piRNA, siRNA, tasiRNA, rasiRNA, 7SK RNA) and parasitic RNA (e.g., retrotransposons, viral genome, viroid, and satellite RNA), and the like. Yet further, the methods can be applied to DNA templates to perform linear amplification of a DNA molecule of interest prior to exponential amplification. For example, the Phi6 polymerase enzyme can use either RNA or DNA molecules having a single-stranded 3' end as templates to synthesize a complementary RNA strand.

While nucleic acids can be cloned prior to preparation according to certain aspects of the present invention, in many cases cloning will not be necessary. In single-molecule sequencing applications, large quantities of nucleic acids are not needed to provide a nucleic acid of interest. Instead, genomic DNA, extracted mRNA, or other nucleic acids can be sequenced directly without an intermediate cloning step. Alternatively, and in certain preferred embodiments, the nucleic acids can be amplified prior to sequencing for one or more amplification cycles. Appropriate amplification methods can include PCR, linear PCR (linear rather than exponential amplification), RT-PCR, RACE (rapid amplification of cDNA ends), LCR, transcription, strand displacement amplification (SDA), multiple-displacement amplification (MDA), rolling circle replication (RCR), those described in U.S. Patent Publication No. 20100081143 (incorporated herein by reference in its entirety for all purposes), or other methods known to those of ordinary skill in the art. Multiple amplification methods may be used to generate a template of interest for further analysis. In certain preferred embodiments, amplification of nucleic acids prior to sequence analysis comprises a combination of amplification techniques, e.g., both linear and exponential amplification.

Procedures for isolating, cloning, fragmenting, ligating, and amplifying nucleic acids are replete in the literature and can be used in the present invention to provide a nucleic acid to be sequenced. Further details regarding nucleic acid cloning, fragmentation, ligation, amplification and isolation can be found in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc ("Rapley"); *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel")); Kaufman et al. (2003) Handbook of Molecular and Cellular Methods in Biology and Medicine Second Edition Ceske (ed) CRC Press (Kaufman); *PCR Protocols A Guide to Methods and Applications* (Innis et al. eds) Academic Press Inc. San Diego, Calif. (1990) ("Innis"); Chen et al. (ed) *PCR Cloning Protocols, Second Edition* (Methods in Molecular Biology, volume 192) Humana Press; in Viijoen et al. (2005) *Molecular Diagnostic PCR Handbook* Springer, ISBN 1402034032; Demidov and Broude (eds) (2005) *DNA Amplification: Current Technologies and Applications*. Horizon Bioscience, Wymondham, UK; and Bakht et al. (2005) "Ligation-mediated rolling-circle amplification-based approaches to single nucleotide polymorphism detection" *Expert Review of Molecular Diagnostics*, 5(1) 111-116. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A plethora of kits are commercially available for the purification of plasmids or other relevant nucleic acids from cells, (see, e.g., EasyPrep™, FlexiPrep™, both from Pharmacia Biotech; StrataClean™, from Stratagene; QIAprep™ from Qiagen). Many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen. For RNA purification, some of these products include the Dynabeads® mRNA Purification Kit (Life Technologies), Absolutely Total RNA and mRNA Purify Kits (Agilent Technologies), polyA Spin™ mRNA Isolation Kit (New England BioLabs), the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), the Easy-mRNA Kit (BioChain), and the NucleoTrap™ mRNA kit (Clontech). Instructions for the use of these and other commercially available kits for nucleic acid isolation/purification are readily available from the manufacturers. Further details on cDNA preparation are provided below.

Any isolated and/or purified nucleic acid can be further manipulated to produce other nucleic acids (e.g., cDNA can be produced using mRNA), used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Sambrook, Ausubel and Berger. In further embodiments, nucleic acids are subjected to fragmentation, e.g., using mechanical methods, such as sonication, mechanical shearing, nebulization, hydroshearing, and the like; enzymatic methods, such as exonuclease digestion, restriction endonuclease digestion, and the like; and electrochemical cleavage, e.g., all methods well known and routinely used in the art. In addition, essentially any nucleic acid can be custom or standard ordered from any of a variety of commercial sources, such as Operon Technologies Inc. (Huntsville, Ala.).

In certain embodiments described herein, amplification of the sample nucleic acid is performed. The most widely used in vitro technique for amplifying nucleic acids is the polymerase chain reaction (PCR), which requires the addition of a template of interest, e.g., a DNA comprising the sequence that is to be amplified, nucleotides, oligonucleotide primers, buffer, and an appropriate polymerase to an amplification reaction mix. In PCR, the primers anneal to complementary sequences on denatured template DNA and are extended with a thermostable DNA polymerase to copy the sequence of interest. As a result, nucleic acids comprising sequence complementary to a template strand to which a primer was bound are synthesized, and these nucleic acids comprise the primer used to initiate the polymerization reaction. Repeated cycles of PCR generate many copies of the template strand and its complement. Other methods of amplifying nucleic acids are known to those of ordinary skill in the art, e.g., RT-PCR, rolling-circle amplification, etc. Certain methods for amplifying nucleic acids in preparation for sequencing are described in detail in U.S. Pat. No. 8,003,330, which is incorporated herein by reference in its entirety for all purposes.

Primers ideally comprise sequences that are complementary to the template. However, they can also comprise sequences having non-complementary, non-canonical, and/or modified nucleotides or sequences including, but not limited to, restriction sites, cis regulatory sites, oligonucleotide hybridization sites, protein binding sites, polymerase promoters, RNA promoters, sample or library identification sequences, combinations of deoxyribonucleotides and ribonucleotides, and the like. Primers can comprise modified nucleotides, such as methylated, biotinylated, or fluorinated nucleotides; and nucleotide analogs, such as dye-labeled nucleotides, non-hydrolysable nucleotides, and nucleotides comprising heavy atoms. Primers comprising such modifications can be custom synthesized, and PCR can be a useful means by which to integrate the modifications into nucleic acids. Specific methods that use primers with modifications are further described below. As noted above, modified, non-canonical, and/or non-natural nucleotides or nucleotide analogs are described in U.S. patent application Ser. No. 12/945,767, filed Nov. 12, 2010, and incorporated herein by reference in its entirety for all purposes. For example, in certain embodiments inclusion of a modification alters the efficiency of hybridization between the primer and the primer binding site and/or creates a recognition site for a further modification of the primer or resulting amplicons, e.g., by an enzyme such as a glycosylase or nuclease. In specific embodiments, ribo- or deoxyribonucleotides within a primer sequence comprise 2' O-methyl-modified sugar groups, and these modified nucleotides increases the melting temperature and the kinetics of hybridization, thereby promoting annealing to the primer binding site and enhancing the stability of the hybridized complex at a wider range of temperatures. (See, e.g., Majlessi, et al. (1998) Nucl. Acids Res. 26(9): 2224-2229, incorporated herein by reference in its entirety for all purposes.) in addition, 2' O-methyl-modified nucleotides are less susceptible to a variety of ribo- and deoxyribonucleases. In certain preferred embodiments, the number of 2' O-methyl-modified nucleotides within a primer is at least about 6, 7, 8, 9, or 10. The modified nucleotides may be adjacent to one another, or spaced apart, and can be located internally or terminally within the primer.

Preparing and Amplifying DNA Molecules Derived from a Single RNA Molecule

In certain aspects, the invention provides improvements to methods of cDNA production and/or amplification. The cDNAs so produced are optionally subjected to further manipulations and/or analysis, e.g., nucleic acid sequencing reactions. Data obtained from sequencing the cDNAs or nucleic acid templates derived therefrom can be useful in identifying various features of the cDNAs, e.g., novel splice variants of a gene of interest or full-length haplotypes, or in comparing differential expression of a gene of interest, e.g., between different tissue types, between different treatments to the same tissue type or between different developmental stages of the same tissue type. For example, the differential expression can comprise varying amounts of a given mRNA, different splice isoforms being expressed, or a combination thereof. Further, loci that are identified as variant positions in the cDNA preparation can be further analyzed to determine if the variant positions were present in the original nucleic acid isolated from the source, or if the variant position was introduced during the cDNA synthesis process.

mRNA can typically be isolated from almost any source using protocols and methods described in, e.g., Sambrook and Ausubel. For example, mRNA can be obtained from a eukaryotic subject or a specific tissue derived from a eukaryotic subject. The yield and quality of the isolated mRNA can depend on, e.g., how a tissue is stored prior to RNA extraction, the means by which the tissue is disrupted during RNA extraction, or on the type of tissue from which the RNA is extracted. RNA isolation protocols can be optimized accordingly. Many mRNA isolation kits are commercially available, e.g., those listed herein supra. In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountain View, Calif.).

In conventional methods, once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in cDNA Library Protocols, I. G. Cowell, et al., eds., Humana Press, New Jersey, 1997, Sambrook and Ausubel. In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services. However, all these conventional methods of cDNA synthesis suffer from the problem that base misincorporations resulting in base sequence changes in the newly synthesized nucleic acids are introduced during the synthesis and/or subsequent amplification, and these unintentional base changes are indistinguishable from the true variants originally present in the sample mRNA molecules.

Briefly, synthesis of cDNA from mRNA involves several steps during which misincorporation events can result. First, an RNA-dependent DNA polymerase (e.g., reverse transcriptase) synthesizes first strand cDNA using the mRNA molecule as a template. The mRNA is subsequently digested, e.g., with RNase, and a second cDNA strand is synthesized using the first strand cDNA molecule as the template by a DNA-dependent DNA polymerase. Typically, the resulting double-stranded cDNA molecule is PCR-amplified using DNA-dependent DNA polymerase to increase the amount of the nucleic acids to be subsequently cloned, sequenced, or otherwise analyzed or manipulated. During any of these polymerase-mediated synthesis reactions, a base incorporation error can occur that will be maintained and propagated throughout the rest of the process and will be proliferated in new nucleic acid strands that are synthesized using the erroneous strand as a template. As such, the errors introduced are not randomized, but rather are replicated in the daughter strands, making it challenging if not impossible to distinguish between introduced base changes and true variant base positions. In particular, any errors introduced during the initial first and second cDNA strand synthesis reactions will be present in all of the subsequently synthesized daughter strands, making them indistinguishable from loci comprising variants that were present in the original mRNA molecule ("true variants").

FIG. 1 provides an illustrative example of how traditional cDNA synthesis results in propagation of errors in the resulting cDNA molecules. An mRNA (dashed line) having a single variant position (open circle), e.g., as compared to a reference sequence, is first treated with a reverse transcriptase to synthesize a first cDNA strand, which maintains the variant position. Due to the finite error rate of the reverse transcriptases, the first cDNA strand has base misincorporations (filled stars) in addition to the original single variant position. After the RNA is digested, e.g., by chemical or enzymatic means, the second strand of the cDNA is synthesized by a DNA-dependent DNA polymerase, which also results in the additional base misincorporation (open star) due to the inherent error rates of DNA-dependent DNA polymerases. PCR amplification of the double-stranded cDNA replicates these strands, thereby maintaining the base misincorporations in the resulting amplicons. Further, additional base misincorporations (filled triangles) occur during the PCR amplification, as well. (Although the second cDNA strand synthesis is shown here as a step that is separate from the PCR amplification, in some methods the second strand synthesis occurs as a first step in the PCR amplification process.) As can clearly be seen from this illustrative example, the proliferation of the misincorporation events introduced in the first cDNA strand synthesis, makes these misincorporation events indistinguishable from the variant position that was present in the original mRNA molecule, and it would not be possible to derive the original mRNA sequence based on the sequences of these amplicons. In contrast, the errors introduced during the PCR amplification are randomly dispersed in the amplicons, so can be identified and corrected during subsequent sequence analysis, e.g., consensus sequence determination. The errors introduced during the second cDNA strand synthesis can, in principle, be distinguished from the original variants since they would be expected to be present in only about half of the final amplicons.

The present invention provides an improvement to the above-described conventional methods, and this improved method randomizes the errors introduced during cDNA synthesis thereby allowing these misincorporation errors to be distinguished from the true, original variants of the sample RNA molecule. It will be understood that these methods are applicable not only to converting mRNA to cDNA, but also to conversion of other types of RNA molecules, e.g., rRNA, tRNA, genomic RNA (e.g., retroviral genomes), ribozyme RNA (e.g., ribonuclease P, ribonuclease MRP, etc.), SRP RNA, tmRNA, snRNA, snoRNA, SmY RNA, gRNA, scaRNA, Y RNA, vRNA, telomerase RNA, spliced leader RNA, regulatory RNA (e.g., antisense RNA, CRISPR RNA, long ncRNA, miRNA, piRNA, siRNA, tasiRNA, rasiRNA, 7SK RNA) and parasitic RNA (e.g., retrotransposons, viral genome, viroid, and satellite RNA). Conversion of sample RNA molecules to cDNA allows various further manipulations that are simpler using a DNA template, e.g., cloning, amplification, and nucleotide sequence analysis, as compared to using an RNA template.

In certain aspects, the methods herein find particular benefit in the determination of the true, original sequence of an RNA molecule from a sample of interest, where the RNA molecule must be converted to DNA, and optionally amplified, prior to sequence analysis. Typically, the concentration of starting RNA is in the nanomolar or picomolar range, e.g., at least around 5 nM, 3 nM, 1 nM, 500 pM, 200 pM, 100 pM, 50 pM, 20 pM, 10 pM, or 5 pM, but can also be lower, e.g., in the femtomolar range. The process involved in the conversion to DNA and amplification reactions can introduce changes in the sequence, e.g., by misincorporation and other mechanisms, and these introduced changes can be difficult or impossible to identify using conventional methods, as discussed above. In some embodiments, a single RNA molecule is converted to DNA and amplified, wherein during these manipulations certain sequence changes occur such that the amplicons produced are not identical. As such, sequencing these amplicons produces sequence reads that can be aligned, but that comprise loci having varying base compositions from read to read. The methods herein provide a strategy for the person of skill to determine the true sequence of the original RNA molecule by identifying the changes that were introduced during the preparation of the amplicons that were sequenced. Similarly, a population of RNA molecules from a sample or source of interest can be analyzed and the true variants present in the population can be distinguished from sequence changes introduced during cDNA synthesis, with our without subsequent amplification. For example, the original population can be a set of mRNA sequences from a single gene in a diploid organism. mRNA transcribed from different homologs can differ, for example, where the genes in the homologous chromosomes are heterozygous (e.g., at SNP loci, in repetitive regions, etc.), or where the splicing of each differs from the other. These differences will be evident in the sequence of the cDNA produced, but additional sequence changes can also be introduced. The methods herein provide a way to distinguish between the true differences between the mRNA species and the differences introduced during processing of the mRNA. Yet further, where RNA species from different samples can be tagged (e.g., using barcode sequences, as described elsewhere herein), multiplexing can allow simultaneous evaluation of RNAs from multiple different sources while still allowing discrimination of true sequence variants from introduced sequence changes; the tags (e.g., barcode sequences) serve to link those sequence reads that originated from a single source so that their nucleotide sequences can be analyzed separately from the nucleotide sequences from other sources. In other words, the resulting sequence reads, generated in a single sequencing reaction, can be grouped into sets based upon the tag carried by each, and each set of sequence reads having the same tag is used to determine a consensus sequence for the original RNA molecule from which they all descended.

Figure 2:
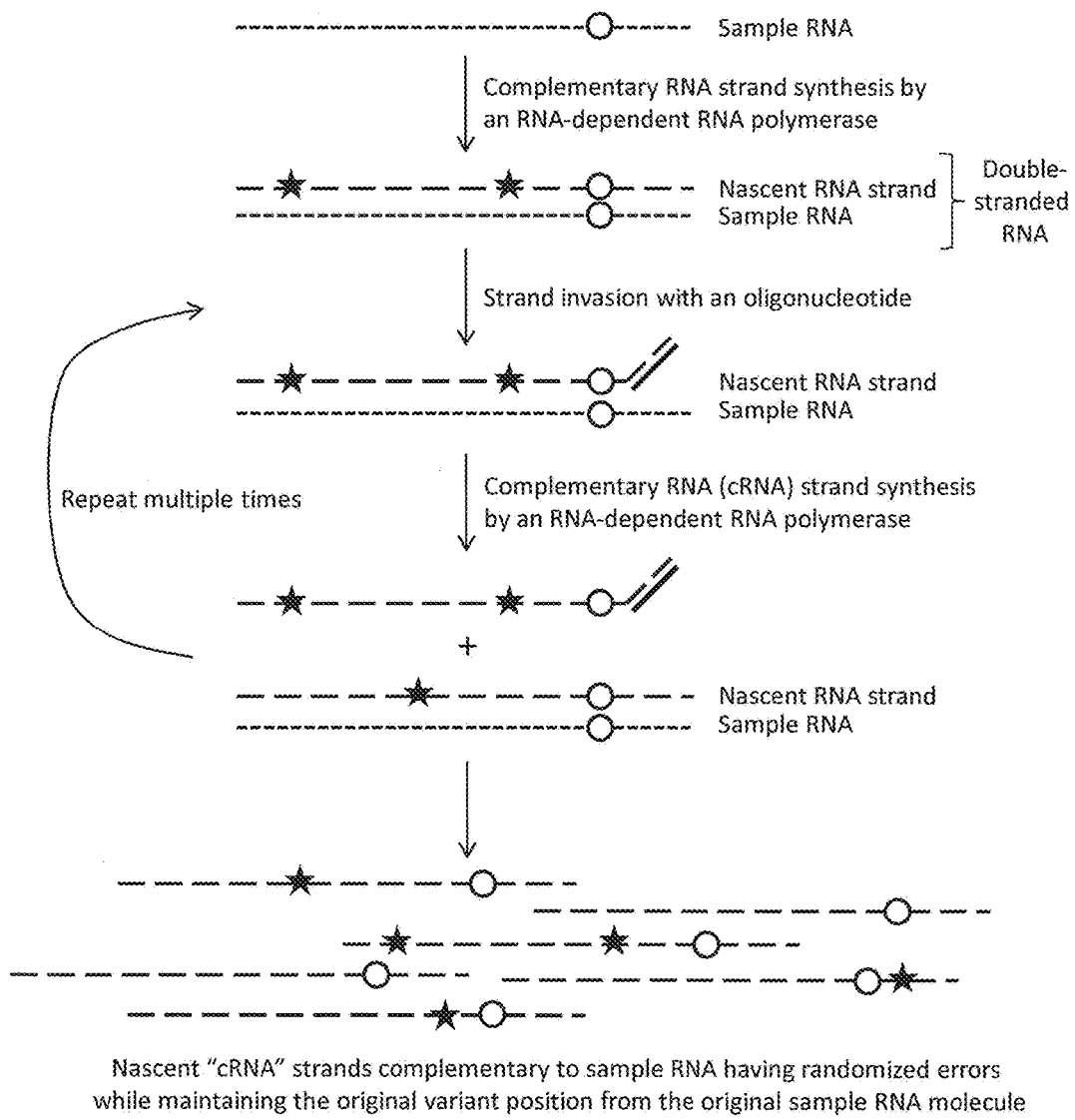
FIG. 2 provides an illustrative example of certain embodiments of the methods provided herein.

FIG. 2 provides an illustrative example of certain embodiments of the methods provided herein. In a first step, the sample RNA molecule comprising a variant position (open circle) is treated with an RNA-dependent RNA polymerase (e.g., Phi6 RNA polymerase from bacteriophage Phi6) to produce a double-stranded RNA molecule comprising the original sample RNA strand and a nascent RNA strand complementary thereto, the latter of which may have base misincorporations (black stars). An oligonucleotide with the ability to strand invade at the end of the dsRNA molecule is added, and this oligonucleotide anneals to the 5' terminal region of the nascent RNA strand, which makes the 3' end of the original RNA strand available once again for a further nascent strand synthesis reaction. The polymerase rebinds to the 3'-end of the sample RNA strand and synthesizes a second, complementary, nascent RNA strand, simultaneously displacing the first nascent RNA strand. Like the first nascent RNA strand, the second, complementary, nascent RNA strand may have base misincorporations (black star), but they will be at different positions than those in the first nascent strand. This linear amplification of the sample RNA molecule is repeated multiple times (e.g., 10-60, more preferably 20-50, and typically about 30 times) to produce a set of complementary, nascent RNA strands, each of which was synthesized using the original sample RNA molecule as the template molecule. Any misincorporation errors that occur in the linear amplification of the sample RNA will be randomly distributed in the daughter nascent strands. However, the variant positions present in the original sample RNA will be present in all the daughter strands. In preferred embodiments, the linear amplification is carried out until at least about 10-, 15-, 20-, 25-, 30-, 35-, 40-, 45-, 50-, 55-, 60-, 65-, or 70-fold molar amplification is achieved. In some preferred embodiments, the reaction is carried out at a constant temperature, e.g., that is different from, and preferably higher than, the optimal reaction temperature of the RNA-dependent RNA polymerase, e.g., 5-10° C. higher. For example, for the Phi6 RNA replicase, the optimal reaction temperature is 32° C., and a temperature of about 39-41° C., preferably 40° C., can be used for the linear amplification reaction. In such embodiments there are no "cycles" to count, as in PCR. As such, the reaction must be given enough time to achieve the fold-amplification desired. This can be determined empirically, or small aliquots can be taken from ongoing reactions and analyzed to determine if the fold-amplification is sufficient, e.g., by gel electrophoretic analysis, optical density measurements, or other nucleic acid quantification methods/instruments known in the art. For example, real-time (RT) PCR can be used to quantify RNA amplification at concentrations lower than the gel detection limits. In other embodiments, the temperature is cycled between the optimum temperature for the Phi6 replicase (e.g., 32° C.) and the optimum temperature for the strand invasion (e.g., about 40° C.) to increase the polymerization rate during nascent strand synthesis. This cycling provides a way to count the cycles and better estimate the fold-amplification at any point in the reaction.

The Phi6 RNA polymerase does not require a primer to initiate synthesis on an RNA template, but it does require a specific initiation sequence at the 3' end of the template. As such, RNA molecules to be subjected to linear amplification using the Phi6 RNA polymerase must comprise this initiation sequence. The present invention provides methods for adding the Phi6 initiation sequence to an RNA molecule to be amplified. The initiation sequence is 5'-UUUUUUUCC-3' and a single-stranded RNA or DNA adaptor comprising this sequence at the 3' terminus can be ligated to the 3' end of an RNA molecule using an RNA ligase, e.g., T4 RNA Ligase 1 or, more preferably, T4 RNA Ligase 2. In preferred embodiments, the 5' end of the adaptor comprising the initiation sequence is adenylated to facilitate ligation to the 3' end of the RNA molecule. Further, it is preferred to have the 3'-C of the adaptor be a dideoxycytidine to prevent adaptor dimerization during the ligation reaction. This dideoxy modification is also beneficial in preventing "self-priming" of the RNA template during the amplification reaction. "Self-priming" is an event wherein the 3'-end of the RNA template folds back on itself to create a site at which Phi6 can initiate, albeit with a much lower efficiency compared to the single-stranded 3'-end. Further, the 5' end of the adaptor can comprise additional sequence motifs, e.g., primer binding sites, restriction enzyme recognition sequences, or, in certain preferred embodiments, barcode sequences, as further described elsewhere herein. The adaptor is present is excess in the ligation reaction (e.g., about 10-fold higher molar concentration relative to the concentration of the RNA sample (e.g., in the picomolar range), and at higher excesses as the concentration of RNA decreases, e.g., into the femtomolar range), and is preferably removed prior to amplification. Various methods can be used to remove the excess adaptor sequence(s) prior to amplification, e.g., gel electrophoresis or commercially available long RNA (>200 nts) purification kits. In certain preferred embodiments, a BluePippin™ platform (Sage Science, Beverly, Mass.) is used and provides a good yield of the RNA-adaptor construct while removing a majority of the excess adaptor sequences that were not subject to ligation.

Figure 3:
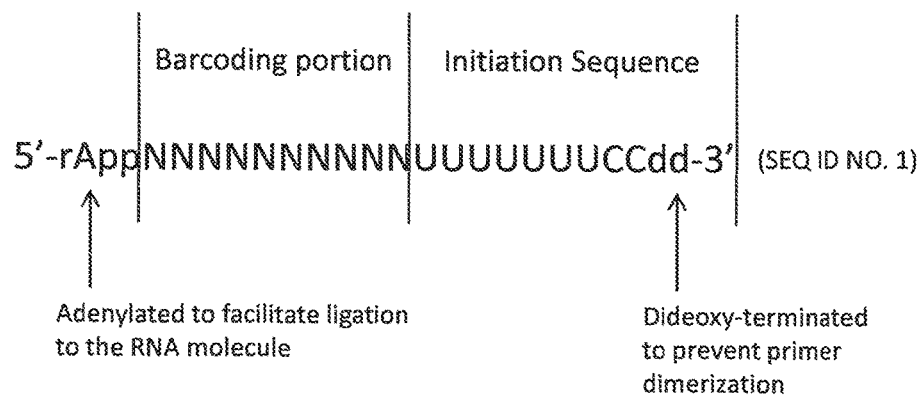
FIG. 3A provides an exemplary illustration of an adaptor comprising both a barcode sequence and a Phi6 initiation sequence.
FIG. 3B provides an illustration of one embodiment of an invading oligonucleotide.
Figure 3:
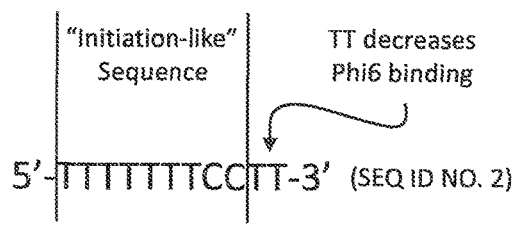

In preferred embodiments, the oligonucleotide with the ability to strand invade at the end of the dsRNA molecule is a locked nucleic acid (LNA). The ribose moiety of an LNA nucleotide is modified with an extra linkage between the 2'-oxygen and the 4'-carbon, thereby "locking" the ribose into the 3'-endo (North) conformation. These nucleotides and oligonucleotides comprising them, either purely or mixed with non-LNA nucleotides, are commercially available. The locked ribose conformation enhances base stacking and significantly increases hybridization properties and melting temperatures of oligonucleotides comprising LNAs. As such, the LNA oligonucleotide used to invade the end of the dsRNA molecule has enhanced hydridization properties and, therefore, stronger binding to the 5'-end of the nascent RNA strand. This strong binding helps to stabilize the opened conformation of the dsRNA end, thereby facilitating the binding of the RNA-dependent RNA polymerase for a subsequent nascent RNA strand synthesis using the sample RNA strand as the template. The 3' end of the invading oligo anneals to the complement of the Phi6 initiation sequence. In some embodiments, the invading oligo is a DNA-LNA oligo with the sequence "TTTTTTTCC-3'" at the 3' terminus, and in other embodiments it is an RNA-LNA oligo with the sequence "UUUUUUUCC-3'" at the 3' terminus. The invading oligo can comprise additional sequence at its 5' end, depending on what is known about the corresponding complementary sequence in the nascent strand to which it must anneal, i.e., either the complementary sequence of the nascent strand or the barcode. In addition, to prevent replication of any unannealed oligo in the reaction mixture during the linear amplification, the invading oligo can be modified to render it unsuitable for Phi6-mediated replication. For example, addition of bases (e.g., thymidine nucleosides) and/or other moieties (e.g., bulky groups, such as biotin, which can be attached to the oligo through a spacer or thymidine residue) at the 3' terminus can mitigate this side reaction. In certain preferred embodiments, the DNA-LNA oligo used in the methods herein comprises the sequence "TTTTTTTCCTT-3'" at the 3' terminus. Optionally, the DNA-LNA oligo is at least about ten nucleotides in length, but can be longer or shorter, as long as it is long enough to bind specifically and robustly to the strand complementary to the initiation sequence.(See, e.g. , SEQ ID NO. 2 FIG.3.)

In alternative embodiments, other strong-binding nucleotides can be used in or as the invading oligo, either instead of or in combination with LNA nucleotides. For example, a peptide nucleic acid (PNA) polymer can be used in the invading oligo. (See, e.g., Nielsen, et al. (1991) Science 254(5037):1497-1500, incorporated herein by reference in its entirety for all purposes.) Due to a higher binding stability and specificity than DNA oligonucleotides, the PNA oligomers generally only need be 20-25 bases long for strong interaction with a complementary DNA or RNA strand. PNAs are also stable over a wide pH range. However, they do have a lower melting temperature than LNAs, so the length of a PNA oligo needs to be longer than that of an equivalent LNA oligo, but not as long as that of a DNA oligo. Alternatively or additionally, other types of nucleotides can be included in the invading oligo. In specific embodiments, ribo- or deoxyribonucleotides within the oligo comprise 2' O-methyl-modified sugar groups, and these modified nucleotides increase the melting temperature and the kinetics of hybridization, thereby promoting annealing to the 5'-terminal region of the strand complementary to the sample RNA strand. 2'-O-methyl-modified nucleotides enhance the stability of the hybridized complex at a wide range of temperatures. (See, e.g., Majlessi, et al. (1998) Nucl. Acids Res. 26(9): 2224-2229, incorporated herein by reference in its entirety for all purposes.) In certain preferred embodiments, the number of 2'-O-methyl-modified nucleotides within an invading oligo is at least about 6, 7, 8, 9, or 10. The modified nucleotides used in an invading oligonucleotide may be adjacent to one another, or spaced apart, and can be located internally or terminally within the oligo, and can comprise a mixture of those described herein and others known in the art to enhance binding stability.

Once the set of daughter nascent RNA strands are synthesized, they can be converted into cDNA molecules by first treating with a reverse transcriptase to generate a first cDNA strand. Since the primer typically used for first strand cDNA synthesis is complementary to the daughter strands, but not the original "mother" strand, only the daughter strands are used as templates in the first strand cDNA synthesis reaction. After first strand synthesis, the RNA strands (including the original RNA strand used in synthesizing the daughter RNA strands) are degraded, and a second cDNA strand is synthesized using a DNA-dependent DNA polymerase. As explained above in the conventional cDNA preparation method, misincorporation errors can be introduced in the first and second cDNA strand synthesis reactions, but these errors will be different for each nascent RNA strand used to generate the cDNA molecules. As such, these errors will also be randomly distributed in the pool of cDNA molecules produced from the set of nascent RNA strands. The pool of cDNA molecules can be further manipulated and/or analyzed, e.g., by cloning, amplification, and/or sequence analysis. Where the cDNA molecules are amplified, e.g., by PCR, additional misincorporation errors may be introduced, but these errors will be randomly distributed in the resulting pool of amplicons.

Since reverse transcriptase requires a primer with a 3'-OH for template-directed synthesis, a primer that anneals to the 3' terminus of the nascent RNA strands is needed for synthesis of the first cDNA strand. The sequence of this primer can be designed based on an available reference sequence for the original RNA sample, e.g., from an mRNA sequence database or look-up table, or prior sequencing of a genome. Alternatively, an adaptor comprising a primer-binding site can be ligated to the 3' end of the nascent RNA molecule, and the ligation can occur either with or without the primer bound to the primer binding site on the adaptor. In preferred embodiments, the original RNA molecules are ligated to adaptors comprising the Phi6 initiation sequence and a 3'-terminal dideoxycytidine, so they are not suitable for ligation with the adaptor comprising the primer-binding site. The original RNA strands lacking the deoxycytidine-linked adaptor will ligate to the primer-binding adaptor, but since they lack the Phi6 initiation sequence they will not have been amplified, e.g., used as templates to create the daughter strands. Any sequence reads that are generated based on these RNA molecules can be filtered out during analysis of the sequencing data. If the practitioner does not wish to create cDNA from molecules in the original RNA sample, that RNA can be treated, e.g., prior to linear amplification, to block ligation at the 3' terminus, e.g., by removal of the hydroxyl group, addition of a blocking group (e.g., dideoxynucleotide) that prevents ligase activity at that end, or addition of an adaptor having a 3' terminus incompatible with a ligation reaction. In yet further embodiments, the primer-binding sequence needed for first strand cDNA synthesis can be introduced by 5'-end ligation of a complementary sequence to the original RNA (mother) strand; as such, the primer-binding sequence will be synthesized at the 3' end of the daughter RNA strand by Phi6 enzyme during the RNA daughter-strand amplification. Further, to ensure that ligation of the adaptor comprising the primer-binding site only occurs at the 3' end of the RNA daughter strands, the adaptors can have 3' ends that are incompatible with ligation to the 5' end of the RNA daughter strands. Alternatively or in addition, the presence of the invading oligo still annealed at the 5' end of the daughter strands can inhibit ligation to that end, e.g., by extending past the 5'-terminal nucleotide of the daughter strand, or by carrying a bulky group that sterically interferes with the ligation reaction.

The primer for second strand synthesis is typically designed to be complementary to the initiation sequence, barcode, and/or other sequence elements in the adaptor added to the 3' end of the original RNA molecule. PCR primers are typically 18-22 bases in length, but can be shorter if they have a high GC content and/or comprise modifications that lower melting temperature. In certain embodiments, it is preferred that the primer used for second strand synthesis (and, optionally, also amplification following cDNA synthesis) not overlap a sequence complementary to the barcode sequence of the adaptor ligated to the 3' end of the original RNA molecule, e.g., since that region is randomized and such overlap would require that the primers also have randomized portions. As such, the 3'-adaptor can comprise a spacer region between the initiation sequence and the barcode sequence so the primer can have a longer, defined (non-random) primer-binding site.

The double-stranded cDNA molecules produced can be subjected to sequencing immediately following second-strand synthesis, or can be subjected to other manipulations, such as cloning or amplification. The synthesis of the first and second cDNA strands can be performed separately from a subsequent amplification step, but in certain preferred embodiments, a "one-step RT-PCR" reaction is performed in which both first- and second-strand synthesis and amplification occur in the same reaction mixture, one after the other.

The same primers used for first and second cDNA strand synthesis can be used for cDNA amplification, or other primers can be used for amplification. For example, amplification primers can be designed to amplify only a portion of the cDNA molecule, e.g., a portion including the barcode region. For example, if primers are available that flank a region of interest within the cDNA, e.g., a particular exon, use of those primers will produce amplicons comprising only that region, which can be further analyzed without all of the sequence that flanked it in the original cDNA molecule. Where a population of RNAs was used to generate the cDNAs, barcode sequences present in the cDNAs are preferably included in the region amplified by the primers, e.g., to maintain the ability to identify the subsets of cDNAs that descended from each of the sample RNA molecules. In alternative embodiments, the initial first and second cDNA strand synthesis discussed at length above are performed using primers that bind at loci that flank a sequence of interest, e.g., a region corresponding to a variable region, a known mutation site, an exon of interest, or other loci of interest to the investigator. For example, the primer for first strand cDNA synthesis would bind to a locus that is outside of, but adjacent to the 3' end of, the sequence of interest in the amplified RNA daughter strands, and the primer for second cDNA strand synthesis would bind to the first cDNA strands at a locus that is outside of, but adjacent to the 3' end of, the sequence of interest in those strands, which are complementary to the sequence of interest in the RNA daughter strands. In yet further embodiments, a full-length cDNA preparation can be aliquoted into different reaction mixtures to separately amplify different regions of the cDNA, e.g., in order to create separate pools of amplicons of a specific region from a plurality of different individuals. The sequence analysis is simplified when it is known that all the sequences generated come from a specific region, and therefore can be aligned with one another. Optionally, and if there is sufficient amplified RNA generated during the linear amplification step, this aliquoting step could be carried out prior to the first and second cDNA strand synthesis to create cDNAs specific for different regions of the RNA molecule in different aliquots prior to cDNA amplification.

Typically, internal primers, whether used in first and second, cDNA strand synthesis, cDNA amplification, or both, are designed based on the known or reference sequences that flank a region of interest in the RNA/cDNA molecules, e.g., from previous sequencing studies or known homologies to related RNAs. As such, the cDNA molecules produced following RNA and/or cDNA amplification with internal primers will comprise only the region delineated by the primer binding sites, and sequence adjacent to that region in the original RNA molecules will not be present. Yet further, these internal primers can optionally comprise sequence tags, e.g., barcodes, for tracking purposes during sequencing. For example, where a primer used for first cDNA strand synthesis has a first barcode and a primer used for second cDNA strand synthesis has a second barcode, the "daughter" cDNA molecules that are produced can be traced back to strand of the original cDNA molecule from which they descended. In other applications, different barcodes can be used in different aliquots of an RNA or cDNA sample to be amplified using different internal primers. In doing so, the sequence reads that result can be grouped according to the specific region that was amplified in each aliquot, which simplifies consensus sequence determination for each region. These are merely exemplary embodiments, and other uses for sequence-tagged primers will be clear to the ordinary practitioner in light of the teachings herein.

Following cDNA synthesis and, optionally, amplification, the resulting double-stranded cDNA molecules can be subjected to further manipulations including, but not limited to, cloning and nucleotide sequence analysis. Nucleotide sequences determined for the amplified cDNA molecules (cDNA library) are subjected to statistical analysis to determine the correct sequence of the original RNA by determining which, if any, variant positions were present in the original RNA, and which were introduced during the cDNA library construction. For example, a base position that is the same in all or nearly all the cDNA molecules likely represents the sequence of the original RNA molecule, where a base position that varies significantly between cDNA molecules in the same pool was likely introduced during the cDNA library prep. In other words, since the original sample RNA molecule is represented by multiple complementary RNA copies prior to the cDNA synthesis and amplification, any misincorporations that occurred during cDNA synthesis, as well as error introduced during the linear amplification of the original RNA molecule, will only be present in a small portion of the total sequence reads, and, as such, are effectively randomized and can be identified and corrected through consensus sequence determination using sequencing reads of the final pool of cDNA molecules. Methods for sequence analysis and consensus sequence determination are provided in the art, e.g., in U.S. Pat. Nos. 8,182,993 and 8,370,079; U.S. Patent Application Publications 2012/0330566 and 2013/0138358; and U.S. Patent Application Nos. 61/993,420 and 62/028,741, all of which are incorporated herein by reference in their entireties for all purposes.

In some embodiments of the methods provided herein, an RNA molecule is subjected to an exponential amplification reaction rather than (or in addition to) a linear amplification reaction. The exponential amplification strategy begins by adding both (1) the initiation sequence to the 3' end of the sample RNA, and (2) a sequence complementary to the initiation sequence to the 5' end of the sample RNA. In certain preferred embodiments, a 3'-dideoxy-terminated and 5'-adenylated initiation sequence is added to the 3' end of the sample RNA molecule using T4 RNA Ligase 2 as described above. In a second step, the 5' end of the RNA molecule is adenylated using T4 RNA Ligase 1. The third step involves T4-RNA-Ligase-2-mediated ligation of the 5' end of the sample RNA molecule to an adaptor that comprises the complement to the initiation sequence at its 5' end and a hydroxyl group at its 3' end. The hydroxyl group at the 5' end of the adaptor inhibits or prevents adaptor dimerization during the ligation reaction. Addition of the complement of the initiation sequence (5'-GGAAAAAAA-3') to the 5' end of the sample RNA molecule provides template sequence for synthesis of the Phi6 initiation sequence at the 3' end of the daughter strand(s) synthesized using the sample RNA strand as the template strand.

Once the adaptors have been added to the ends of the RNA molecule, the steps in exponential amplification are very similar to those of the linear amplification method. The single-stranded sample RNA is converted to dsRNA using Phi6 polymerase, and the resulting dsRNA molecule is exposed to a strand-invading oligonucleotide to open the end of the dsRNA molecule to re-expose the 3' end of the sample RNA strand. In certain embodiments, the adaptor ligated to the 3' end of the original RNA molecule comprises additional unique sequences at its 5' end that results in complementary unique sequence in the nascent strand, and this complementary unique sequence is not found in the adaptor ligated to the 5' end of the original RNA. This allows the artisan to use a strand-invading oligonucleotide that is complementary only to the end of the double-stranded RNA molecule corresponding to the 3' end of the original RNA molecule. During hybridization of the oligo and subsequent synthesis of the second, complementary, nascent RNA strand, the first complementary strand is displaced. However, unlike the linear amplification method, the first complementary strand has an initiation site for Phi6 at its 3' end, i.e., due to the addition of the adaptor having the complement of the initiation sequence to the 5' end of the sample RNA strand (supra). As such, the first complementary strand, and any other strand synthesized using an RNA template molecule having the sequence of the 5'-terminal adaptor, will have the Phi6 initiation sequence at its 3' end and, as such, will be able to serve as a template for Phi6-dependent dsRNA synthesis, after which the resulting dsRNA molecule can be opened to allow the polymerase access to the initiation site at the 3' end of the newly synthesized strand in the same manner as the first-formed dsRNA molecule was opened, i.e., by annealing of the invading oligo. Therefore, after the synthesis and displacement of the first, complementary, nascent RNA strand, Phi6 polymerase enzymes will bind to both displaced nascent RNA strands and dsRNAs having an invading oligo annealed to reveal a single-stranded 3' end, and complementary nascent strands will be synthesized from both types of templates. As such, the sample RNA molecule is exponentially amplified during the reaction. In alternative embodiments, the adaptor ligated to the 5' end of the original RNA molecule also comprises unique sequence complementary to a strand-invading oligo. The unique sequences in the adaptors can correspond to the same strand-invading oligo, or to two different strand-invading oligos. In such embodiments, an invading oligo binds to each end of each dsRNA molecule to provide Phi6 polymerase with access to the 3' terminus of both strands in the duplex, each of which will serve as a template for simultaneous synthesis of the complementary strands to generate two dsRNA molecules from a single dsRNA molecule. In alternative embodiments, the above-described exponential amplification reaction can be performed after subjecting a sample RNA to a linear amplification in order better randomize any misincorporation events that occur in the exponential amplification. Once the dsRNA amplification is completed, the resulting dsRNA amplicons can be converted to cDNA as described above.

As noted above, the unique sequence complementary to an invading oligo is typically an additional defined sequence at the 5' end of the adaptor comprising the Phi6 initiation sequence that is ligated to the 3' end of the original sample RNA. In some cases, the adaptor comprising the complement to the initiation sequence that is ligated to the 5' end of the original sample RNA does not have sequence complementary to that additional defined sequence, and in other cases the adaptor comprising the complement to the initiation sequence that is ligated to the 5' end of the original sample RNA also comprises a complement to the additional defined sequence at its 3' end. For example, as described below in greater detail, a barcode sequence can be included in the adaptor having the initiation sequence, but the complement to that barcode would not be included in the 3' portion of the adaptor ligated to the opposite terminus of the RNA that has the complement to the initiation sequence, or, optionally, it would be. Additional details of and applications for barcodes are further described below and elsewhere herein. Once the cDNA has been synthesized, the cDNA can subjected to further procedures, e.g., amplified, cloned, etc., as further described elsewhere herein or by conventional methods known to those of ordinary skill in the art.

Barcodes

In certain aspects of the methods described herein, barcodes are included in the adaptor(s) linked to one or both ends of a sample RNA molecule. For example, a barcode in a first adaptor ligated to one end of an RNA molecule may also be present in a second adaptor ligated to the opposite end of the RNA molecule, or, optionally, the second adaptor can comprise a sequence complementary to the barcode, a barcode different from and not complementary to that in the first adaptor, or no barcode sequence at all. Addition of a barcode that is later identifiable, e.g., by sequence analysis, allows the investigator to identify the set of daughter strands, e.g., in cDNA molecules, that came from (directly or indirectly) the same original RNA molecule, i.e., all the strands that were synthesized using either the original RNA molecule, or "descendent" strands (e.g., amplicons) thereof, as a template. Such descendent strands include daughter, granddaughter, great-granddaughter, etc. strands of the original RNA. In doing so, the investigator can specifically compare sequence data from descendent strands of a single initial RNA molecule to determine the nucleotide sequence of that initial molecule. This is particularly beneficial when a heterogeneous population of original RNA molecules are being simultaneously analyzed, e.g., in a single reaction mixture. For a population of non-identical RNA molecules in a sample, barcoding each molecule with a distinct and identifiable barcode allows sequence data collected from amplicons derived from each original RNA molecule to be distinguished from amplicons of other RNA molecules in the mixture. Once identified, the sequences that correspond to a single, original RNA molecule are used to determine the sequence of that single, original RNA molecule. For example, transcription of both genes in a heterozygous individual can produce a population of mRNA molecules comprising mRNA molecules from the first homolog of the gene having a first sequence, and mRNA molecules from the second homolog of the gene having a second sequence. It is likely that these two different mRNA sequences are highly similar, and may only differ at one or a few loci, and these differences may be single nucleotide changes (e.g., substitution, deletion, insertion, etc.) or larger sequence variations (e.g., inversions, recombinations, translocations, differences in posttranslational modification, such as splicing variations, etc.). Further, the abundance of a first transcript can be much greater than that of a second transcript. In some cases, it can be complicated or even impossible to definitively determine the sequences of both homologs from a mixture of sequence reads from both mRNA species, especially where one of the mRNAs is expressed at a low level relative to the other or where the sequence differences between the two are very minor. For example, if all the mRNA sequences are analyzed together, the calls at variant loci in the mRNA present at low levels may be interpreted as miscalls and discarded. By adding a different barcode sequence to each original mRNA molecule, all the sequence reads from the amplicons from each of the mRNA molecules can be identified and used to determine the original sequence for only that "parental" mRNA molecule. This greatly simplifies the sequence analysis and facilitates identification of loci that vary between the two original mRNA transcripts, regardless of their ratio in the mixture. This strategy is also useful for analyzing other types of heterogeneous RNA populations, many of which have far more than two RNA sequences in the original sample. Examples of such heterogeneous RNA samples include whole mRNA, metagenomic analyses, and viral populations. For example, viruses like HIV have some of the highest mutation rates known—and this high mutation rate means that HIV evolves quickly. Infected organisms typically have many different variants of the virus present at any given time. By barcoding a viral population prior to cDNA preparation by the methods herein, the practitioner can determine sequence information for each individual viral genome subjected to the amplification and sequence analysis, and even get a measure of how much of each type of virus is present in the sample. These and other uses of these methods are described at length elsewhere herein.

In preferred embodiments, barcode sequences are included in the adaptor comprising the Phi6 initiation sequence, e.g., where the barcode is at or proximal to the 5' end of the adaptor. FIG. 3A provides an exemplary illustration of an adaptor comprising both a barcode sequence and a Phi6 initiation sequence. The "N" positions indicate randomized positions in the barcode. Preferably, the randomized portion of the barcode should be long enough to ensure that each sample RNA molecule is tagged with a different barcode sequence. The 10-position randomized portion depicted in FIG. 3A would occur by chance only once in $4^{10}$ (1,048,576). Both the dideoxycytidine and adenylated 5' end are also shown in the figure. FIG. 3B provides an illustration of one embodiment of an invading oligonucleotide. The oligo comprises thymine bases instead of uracil bases in what would otherwise be a Phi6 replicase initiation sequence. Two additional thymidine nucleosides are included at the 3'-end to further mitigate binding of Phi6 replicase to the oligo since an initiation sequence having two terminal thymine nucleosides at the 3'-end is a poor initiation sequence. In some embodiments, additional moieties can be included at the 3'-end of the invading oligo, either with or without the two terminal thymine nucleotides. For example, a biotin molecule can be added to the 3-end of the initiation sequence, or added to the two terminal thymidine nucleosides, if they are present. Other groups could also be used, as long as they do not interfere with the strand invasion of the oligo into the dsRNA.

Barcodes for use in the methods herein are, in some embodiments, one of two general types: (1) alternating purines and pyrimidines, $(R/Y)_n$ where R is purine and Y is pyrimidine, and (2) completely degenerate barcodes $(N)_n$ where N stands for any of the four canonical nucleotides. The former are have the benefit of lacking homopolymer repeats, which can be difficult to sequence, but the latter type includes a greater number of possible barcodes per length of barcoding sequence. In some embodiments, a barcode is a hybrid of both types, with some alternating purines and pyrimidines, and some degenerate positions, e.g., where highly unique barcodes are needed that cannot be created using only alternating purines and pyrimidines.

The unique barcoding calculations assume that the probability of a barcode being ligated to a molecule be uniform across all barcodes in the mixture. So, if you have 100 barcodes, the probability of a particular barcode being ligated should be 1/100. For a 40 nts long $(R/Y)_n$ barcode (i.e., n=20), there will be about 1 trillion unique barcode sequences. If you randomly choose 30,000 barcodes from this pool of 1 trillion, then the probability that you choose the same barcode twice is 1e-03 (i.e., the probability that you label two molecules with the same barcode). Similarly, with a 24 nts long $(R/Y)_n$ barcode, one can reliably barcode 183 unique molecules. Or with a 31 nts long $(R/Y)_n$ barcode, one can reliably barcode 2072 unique molecules. Alternatively, if completely degenerate barcodes using $(N)_n$ (i.e., n=40) rather than $(R/Y)_n$ (n=20 for fair comparison) are used, then even more unique barcodes are possible, but so are homopolymer regions. For example, a 24 nts long $(N)_n$ barcode can reliably barcode 750,000 unique molecules, and a 31 nts long $(N)_n$ barcode can reliably barcode 96,000,000 unique molecules.

In general, if one has T total number of distinguishable barcodes, N random pulls (i.e., number of molecules in the sample), and P probability of duplicate hits (i.e., the maximum acceptable probability that you label two molecules with the same barcode), then the relationship is approximated by:

$$N \sim = \mathrm{sqrt}(-2*\ln(1-P))*\mathrm{sqrt}(T)$$

For 24 and 31 nts $(R/Y)_n$ barcodes (logs are base e):

$$183.2245 = \mathrm{sqrt}(-2*\log(1-1e-03))*\mathrm{sqrt}(2^{\wedge}24)$$

$$2072.949 = \mathrm{sqrt}(-2*\log(1-1e-03))*\mathrm{sqrt}(2^{\wedge}31)$$

$(R/Y)_n$ barcodes having about 40 nts will label ~30,000 molecules:

$$23,452.74 = \mathrm{sqrt}(-2*\log(1-1e-03))*\mathrm{sqrt}(2^{\wedge}38)$$

$$33,167.18 = \mathrm{sqrt}(-2*\log(1-1e-03))*\mathrm{sqrt}(2^{\wedge}39)$$

$$46,905.47 = \mathrm{sqrt}(-2*\log(1-1e-03))*\mathrm{sqrt}(2^{\wedge}40)$$

Using the $(N)_n$ barcode bases:

$$750,487.6 = \mathrm{sqrt}(-2*\log(1-1e-03))*\mathrm{sqrt}(4^{\wedge}24)$$

$$96,062,411 = \mathrm{sqrt}(-2*\log(1-1e-03))*\mathrm{sqrt}(4^{\wedge}31)$$

Based on these guidelines and calculations, and general skill in the art, the ordinary practitioner will be readily able to determine both the type and length of the barcodes needed for barcoding a mixture of sample molecules.

Sequencing of a Pool of Double-Stranded cDNA Molecules Generated from a Single RNA Molecule or a Set of RNA Molecules One of the primary benefits of the methods herein is to provide templates for nucleotide sequence analysis that can be used to determine a nucleotide sequence of an original RNA molecule from a sample of interest. The amplified nucleic acids produced can serve as sequencing templates in many different types of sequencing systems, e.g., Sanger sequencing systems, capillary electrophoresis systems, Ion Torrent™ systems (Life Technologies), and MiSeq® and HiSeq® systems (Illumina, Inc.). Preferably, such sequence analysis is performed using a technology that can produce sequence reads from single template molecules, such as nanopore-based sequencing, e.g., from Oxford Nanopore or Genia Technologies. One particularly preferred technology is SMRT® Sequencing from Pacific Biosciences (Menlo Park, Calif.), which is described in detail in the art, e.g., in U.S. Pat. Nos. 7,056,661, 6,917,726, 7,315,019, and 8,501,405; Eid, et al. (2009) Science 323:133-138; Levene, et al. (2003) Science 299:682-686; Korlach, et al. (2008) Nucleosides, Nucleotides and Nucleic Acids 27:1072-1083; and Korlach, et al. (2010) Methods in Enzymology 472:431-455, all of which are incorporated herein by reference in their entireties for all purposes. Briefly, SMRT® Sequencing is a real-time method in which a single polymerase-template complex is observed during template-directed synthesis of a complementary nascent strand. Unlike conventional "flush-and-scan" sequencing methods, the SMRT® Sequencing reaction involves processive strand synthesis by the polymerase, without the need for buffer exchange in between successive base incorporation events. Nucleotide analogs present in the sequencing reaction mixture comprise optically detectable labels (typically fluorescent dyes), which are linked to the analogs at a phosphate group that is removed during incorporation of the nucleoside portion into the nascent strand. As such, the nascent strand produces is "natural" and contains no fluorescent dyes, which diffuse away into the reaction mixture after the incorporation event. During the reaction, the polymerase-template complex is immobilized in an optical confinement called a "zero-mode waveguide" that significantly reduces the background fluorescence to facilitate detection of individual incorporation events. Since SMRT® Sequencing produces sequence reads from a single template molecule, the presence of a barcode allows individual sequence reads to be correlated to a single, parental RNA molecule.

In certain embodiments, a template used in SMRT® Sequencing can be modified to facilitate redundant or iterative sequencing of the same template molecule (or portions thereof) multiple times in a single-molecule sequencing reaction. In certain preferred embodiments, the template molecule is modified by addition of hairpin or stem-loop adaptors at both ends, which produces a molecule that is structurally linear due to the binding between the two strands of the original duplex, but that has no free 5' or 3' terminus and is therefore topologically circular. As such, a circular, a single-stranded template is constructed from a linear, double-stranded fragment such that the resulting circular construct comprises both strands of the double-stranded fragment in a single contiguous strand. Such templates are termed "SMRTbell™ templates" herein, and such templates and derivations thereof are described in detail in Travers, et al. (2010) Nucl. Acids Res. 38(15):e159; and U.S. patent application Ser. No. 12/413,258, filed Mar. 27, 2009; Ser. No. 13/019,220, filed Feb. 1, 2011; and Ser. No. 12/982,029, filed Dec. 30, 2010, the disclosures of all of which are incorporated herein by reference in their entireties for all purposes.

SMRTbell™ templates provide a strategy for generating redundant sequence information during sequencing-by-synthesis reactions, both as a result of generating sequence information for both strands of the original double-stranded nucleic acid, but also by repeatedly or iteratively sequencing the entire template. For example, a single polymerase enzyme with strand displacement activity can initiate at a single position (e.g., at a primer) and synthesize a nascent strand that is complementary to the template; after passing around the template one time, the polymerase can continue around repeatedly, displacing the nascent strand from the template in front of it, to produce a long, concatemeric nascent strand comprising multiple complementary copies of the template. By monitoring nucleotide incorporation into the concatemeric nascent strand, multiple sequence reads are generated for both strands of the original double-stranded fragment. The adapter sequences used to construct SMRTbell™ templates preferably comprise specialized sequences, such as primer binding sites, and regions of internal complementarity to provide a short, double-stranded "stem" region that forms a double-stranded terminus appropriate for ligation to the end of a double-stranded nucleic acid fragment. The portion of the SMRTbell™ template adapter that is not within the stem region is sometimes referred to as the "single-stranded portion" or the "loop" in a stem-loop adapter. SMRTbell™ template adapters may also comprise sequences that regulate polymerase activity (e.g., causing the polymerase to pause or stop). SMRTbell™ template adapters typically comprise canonical nucleotides, but can also comprise non-canonical or modified bases, such as those described in U.S. patent application Ser. No. 12/945,767, filed Nov. 12, 2010. For example, in some embodiments one or more nucleotides having a 2' O-methyl-modified sugar group are included in the adapter sequence. Similar to including these modified nucleotides in primer sequences as described supra, inclusion of these modified nucleotides in an adapter sequence within a primer binding site increases both the melting temperature and kinetics of primer binding, thereby enhancing stabilization of the template-primer complex. An additional feature beneficial to certain embodiments is that the presence of 2' O-methyl-modified nucleotides in the template sequence is inhibitory for polymerase synthesis, and can block progression of the enzyme. (See, e.g., Stump, et al. (1999) Nucl. Acids Res. 27(23):4642-4648, which is incorporated herein by reference in its entirety for all purposes.) In practice, several consecutive 2' O-methyl-modified nucleotides in the single-stranded portion of the SMRTbell™ template adapter provide efficient cessation of nascent strand synthesis, and in preferred embodiments the number of consecutive 2' O-methyl-modified nucleotides is at least about 6, 7, 8, 9, or 10. In alternative embodiments, the adapter comprises deoxyuracils and is treated with uracil deglycosylase to create abasic sites that also serve to terminate polymerization. (See, e.g., U.S. Ser. No. 12/982,029, filed Dec. 30, 2010.) Other modified bases can also be used to terminate polymerization, e.g., locked nucleic acids, 2'-fluoro-modified nucleotides, and the like. In some embodiments, this feature is useful where one wishes to only sequence a single strand of the original, double-stranded fragment. Since often a SMRTbell™ template has the same adapter at both ends of the double-stranded fragment, a polymerase binding at a primer bound to one adapter (at a position over or downstream of the 2' O-methyl-modified nucleotides) will initiate synthesis and process a first strand, but will terminate synthesis at the 2' O-methyl-modified nucleotides within the second adapter sequence. Alternatively, where only one SMRTbell™ adaptor on a SMRTbell™ template has a primer binding site and a termination site, the polymerase can bind and process the entire template (both strands) one time before encountering the termination site to produce a read having both the sense and antisense strand sequences.

In certain embodiments, it is desirable to sequence a full-length cDNA in a single-molecule sequencing reaction to produce a sequencing read that spans the entire length of the cDNA. Poly-A tails, which can be greater than 100 nucleotides in length, play a critical role in the stability of mRNA transcripts, regulate the occupancy of the mRNAs in the translating ribosomes, and are believed to play important roles in cancer and regulation by microRNAs. Methods for generating cDNA templates from full-length mRNA molecules (including the poly-A tails) is described at length in U.S. Patent Application Publication No. 2012/0196279, which is incorporated herein by reference in its entirety for all purposes. The methods described herein can be used in combination with strategies for isolating full-length cDNAs to provide a full-length cDNA library in which the errors are randomized.

In preferred embodiments, mRNA molecules are removed or purified from a sample source (e.g., cell culture, tissue sample, etc.), and a 5'-activated adaptor having a dideoxy 3' end, a Phi6 initiation site, a sequence complementary to a binding site for an invading oligonucleotide (which may include or overlap the Phi6 initiation site), and preferably a unique barcode sequence is ligated to each of the 3' termini of the poly-A tails. Optionally, it can include other sequence elements, e.g., restriction sites, modified bases, structural moieties, or other modifications. In preferred embodiments, T4 RNA Ligase 2 (New England BioLabs, Ipswich, Mass.) is a preferred ligase for this reaction. The mRNA is converted to dsRNA by Phi6 replicase, and addition of the invading oligo allows reprocessing of the original mRNA by Phi6 replicase with a concomitant removal of the first nascent RNA strand. This process is carried out to provide a linear amplification of the mRNA molecule by creating multiple copies of its sequence complement. These sequence complements are then converted to cDNA by using a reverse transcriptase to synthesize DNA strands complementary to the sequence complements, degrading the sequence complements with an RNase enzyme (RNaseH or another appropriate RNA-specific nuclease), and synthesizing a second DNA strand complementary to the first. The resulting "second" cDNA strands are complementary to the original, full-length transcript.

In some embodiments, the method further comprises selection of the first strand of the full-length cDNA, e.g., using an antibody or other protein specific to the 7 mG cap (e.g., eukaryotic translation initiation factor 4E, or eIF4E). This is typically performed prior to second cDNA strand synthesis. Further, synthesis of the second cDNA strand is generally preceded by ligation of an adaptor to the 3' end of the newly synthesized cDNA strand to provide a DNA polymerase primer binding site. Similar to the adaptor ligated to the 3' end of the mRNA transcript, this adaptor can include other sequence elements, e.g., restriction sites, modified bases, structural moieties, or other modifications. The full-length double-stranded cDNA molecule can be optionally selected using an antibody or other protein specific to the 7 mG cap to isolate full-length cDNA products of the reverse transcription reaction. In other embodiments, a size selection by gel filtration can be performed to select for long or full-length double-stranded cDNA products.

Where it is desirable to sequence the full-length cDNA, the selected molecules can be directly sequenced without further amplification, or can be optionally amplified prior to sequencing. Such an amplification is typically directed against the adaptors at each end. The amplification is typically an exponential amplification, but linear amplification, or a combination of linear followed by exponential amplification, is also contemplated. The full-length, double-stranded cDNA molecules, optionally amplified, are used to synthesize SMRTbell™ templates, as described elsewhere herein, for use in single-molecule, real-time, template-directed sequencing (e.g., SMRT® Sequencing), as further described supra. In addition, this single-molecule, real-time sequencing methodology is capable of producing long sequencing reads, e.g., at least about 500, 1000, 5000, 10,000, 20,000 bases or longer. As such, full-length mRNA sequence can be generated in a single sequencing read, e.g., by the action of a single polymerase enzyme on a single cDNA sequencing template (e.g., a SMRTbell™ template comprising a full-length cDNA sequence).

Embodiments Of Specific Applications

Identification of mRNA Variants —The methods herein provide a reliable method for determining a highly accurate consensus sequence for an RNA sample. Traditional methods introduce sequence changes during first and second cDNA strand synthesis ("cDNA conversion"), and these changes are indistinguishable from the true sequence of the original RNA molecule. In certain aspects, the methods herein provide a way to randomize the sequence changes introduced during cDNA conversion by including a linear RNA amplification step prior to the cDNA conversion steps. The linear amplification produces complementary copies of the original RNA molecule, and any errors introduced during this amplification will be randomly distributed within the pool of daughter strands produced, which are subsequently subjected to cDNA conversion. In doing so, any errors introduced during the cDNA conversion are randomized within the plurality of cDNA amplicons produced since a plurality of cDNA conversions are effectively carried out for each single sample RNA molecule. The cDNA amplicons are subjected to a sequencing reaction, and the sequence reads generated are analyzed to determine a consensus sequence for the original sample RNA molecule. The sequence changes introduced during the various steps are easily identified since they are randomly distributed in the cDNA amplicons sequences, and can therefore be corrected during sequence analysis. Further, in preferred embodiments, each sample RNA molecule is linked to a barcode sequence that is replicated in the linear amplification, cDNA conversion, and cDNA amplification such that cDNA sequence reads generated during the sequencing reaction can be linked back to an original sample RNA, and those reads that are identified as descendants of the same RNA molecule are analyzed together to determine the sequence of the RNA molecule and to identify sequence changes that were introduced during the process and are, therefore, did not originate in the original RNA molecule. This method facilitates both resequencing efforts, in which a reference sequence is available for comparison to the sequence reads generated, as well as for de novo sequencing, in which there is no reference sequence available.

Analysis of Viral Populations—Viral RNA genomes exhibit high levels of variability due to high mutation rates inherent to viral replication systems. In particular, viral polymerases exhibit high error rates during replication and typically produce replicated strands comprising one or more point mutations, e.g., substitution errors. These point mutations are randomly distributed along the viral RNA genome. Yet further, a high probability for recombination exists during viral replication, and this provides the virus with a ready mechanism for genome diversification. For example, a viral polymerase may begin replication on a first viral RNA, and then switch to a second viral RNA before reaching the end of the first strand. The resulting nascent RNA strand will be composed of sequence originating from both parental strands.

In conventional methods, viral RNAs are not typically sequenced directly. Most commonly, they are first barcoded and converted to cDNAs using reverse transcriptase. cDNAs are subsequently amplified by PCR, and the PCR products are sequenced using standard, usually ensemble, methods. This sample preparation does not allow reliable detection of point mutations in the original population of viral RNAs because the errors that are introduced during the cDNA synthesis reaction are not randomized and cannot be distinguished from the point mutations in the viral RNAs. In other words, although the sequence of the cDNAs will, for the most part, contain the point mutations in the viral RNA, they will also contain mutations introduced during the cDNA synthesis reaction, and these two types of mutations will not be able to be distinguished from one another during sequence analysis.

By performing a linear RNA amplification prior to cDNA synthesis, a single viral RNA is barcoded and copied into many complementary RNAs, each of which may have a mutation due to replication error, but these mutations will be randomized in the resulting pool of RNA amplicons. These (mostly) complementary RNAs are converted into cDNAs, and this process will also introduce some number of mutations due to replication error. Sequencing of the cDNAs will produce sequence reads having point mutations from the original viral samples, mutations introduced during the RNA amplification, and mutations introduced during the cDNA synthesis and amplification. However, the presence of the barcode sequences allows the sequence reads to be grouped according to which original viral RNA each was descended. Aligning and comparing the sequences that all originated with a single viral RNA will reveal point mutations present in the viral RNA since these will be present in all (or nearly all) the sequence reads, whereas the mutations introduced during the earlier steps of the method will be randomized and easily identifiable as not having been present in the viral RNA "parent" molecule.

Metagenomic Analysis—The methods and compositions provided herein are ideally suited for multiplex analyses, and in particular, metagenomic analyses. In such methods, multiple different RNA molecules are present in a single sample, and often at low concentrations. These methods will allow the generation of accurate consensus sequence determination for the plurality of different starting RNA molecules by attaching barcodes to the sample RNAs and randomizing the error by performing a linear amplification of the RNAs prior to cDNA synthesis, amplification, and sequence analysis. For example, whole mRNA from a cell or tissue can be analyzed in this manner, and sequence can be generated from not only the abundant RNA species, but also from those present at lower levels. Environmental samples can be analyzed to identify microbes present, e.g., viruses and bacteria, simply by analyzing the RNA sequences present and comparing them to a database of reference RNA sequences for microbial species. Forensic analysis can also benefit from this method, especially where the source for the starting RNA material contains RNA from many different individuals. Still further, analysis of microbial populations within an organism, e.g., populations in the stomach, intestines, mouth, nose, or on the skin, will benefit from the methods and compositions provided by the instant invention.

EXAMPLES

Linear Amplification of RNA Molecules

In a first step, an RNA oligonucleotide adaptor comprising a random sequence at the 5'-end ("barcoding portion") and the initiation sequence for the Phi6 RNA-dependent RNA polymerase (UUUUUUUUCC-3'; SEQ ID NO. 3) at the 3'-end was acquired from Integrated DNA Technologies (Coralville, Iowa). The adaptor was subjected to phosphorylation at its 5'-end and dideoxy-termination at the 3'-end. The phosphorylated and dideoxy-terminated adaptor was adenylated at the 5'-end in a reaction mixture (100 µl) comprising 1 u/µl RNA Ligase 1 and the corresponding buffer (New England BioLabs, Ipswich, Mass.), 1 mM ATP, 100 µM adaptor, and 6% PEG 8000. The reaction mixture was incubated at 37° C. for 30 minutes, followed by addition of 4 µl of 0.5 M EDTA. The adenylated adaptor was precipitated by addition of ammonium acetate to a final concentration of 3 M and subsequent addition of 0.5 µl glycogen and 2.5 volumes of absolute ethanol. The precipitation was carried out at −30° C. for at least one hour, and followed by centrifugation at 14,000 rpm at 4° C. The supernatant was removed and the obtained pellet washed 2× with 500 ul of 70% ethanol. After the last wash, the pellet was dried on air and dissolved in Milli-Q® Type I ultrapure water.

To ensure the RNA sample has a 3'-hydroxyl group appropriate for ligation to the adaptor, it was subjected to treatment with polynucleotide kinase (PNK), which eliminates any phosphate groups from the 3'-end of the RNA. The reaction mixture (100 µl) comprised 0.40 µM of the RNA sample, 0.10 u/µl of T4 PNK (USB/Affymetrix, Santa Clara, Calif.), and the same RNA Ligase 1 buffer used in the adenylation reaction described above. The reaction mixture was incubated at 37° C. for 30 minutes prior to addition of 4 µl of 0.5 M EDTA per 100 µl of reaction volume. The PNK was subsequently deactivated at 65° C. for 10 minutes. The resulting mixture was taken directly into the ligation reaction below. (Lower concentrations of RNA sample have also been used successfully. For example, 5 nM and 200 pM have been subjected to this methodology to generate highly accurate sequence reads (data not shown).)

Figure 4:
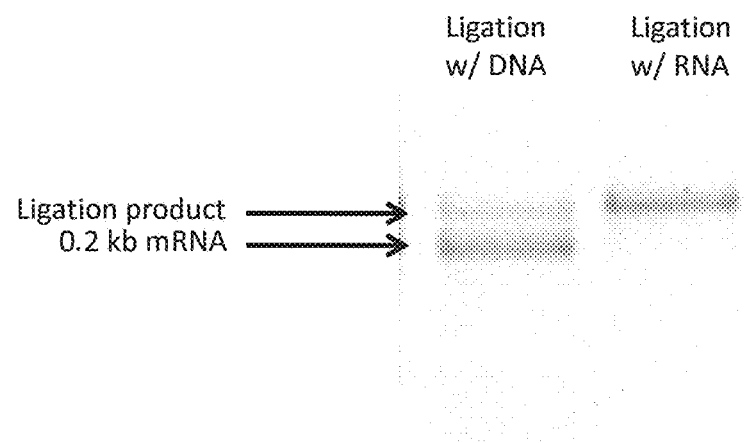
FIG. 4A provides an image of a gel containing the products of ligation reactions using either DNA or RNA adaptors, and FIG. 4B provides a graphical representation of these results.
Figure 4:
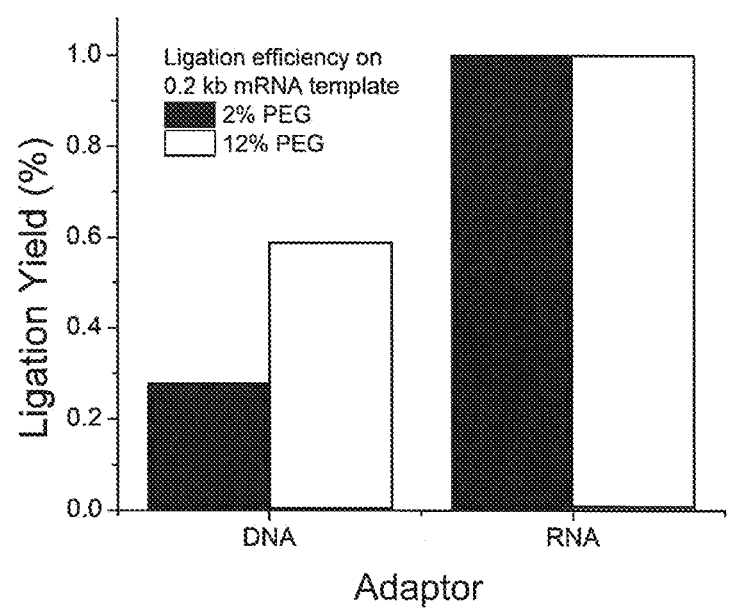

After PNK deactivation, the adaptor was ligated to the PNK-treated RNA in a reaction mixture (200 µl) comprising the PNK-treated RNA, T4 RNA Ligase 1 buffer, 10 mM $MgCl_2$, 12% (w/v) PEG 8000, 0.5 u/ml SUPERase-In™ RNase inhibitor (Ambion/Life Technologies, Foster City, Calif.), 3.8 µM of the adenylated RNA adaptor, and 10,000 u/ml of T4 RNA Ligase 2, truncated K227Q (New England BioLabs, Ipswich, Mass.). This mixture was incubated at 25° C. for four hours. After the incubation, the products of the ligation were purified using the RNeasy® Mini Kit (cat. #74104; Qiagen, Venlo, Netherlands), followed by fractionation using the BluePippin™ platform (Sage Science, Beverly, Mass.), when the RNA+adaptor fraction is collected at appropriate elution times, which depend on RNA+adaptor length and gel concentration and are determined empirically by standard laboratory methods. (One exemplary method for making this determination is described in the following Example.) This ligation reaction was tested using either DNA or RNA adaptors, and the ligation efficiency was found to be higher with the RNA adaptor. In fact, the yield of the ligation reaction using the RNA adaptor was found to be ~100%. A gel and graphical representation of these results are shown in FIGS. 4A and 4B.

Linear amplification with the purified mRNA+adaptor constructs (templates) was performed in a 20 µl reaction mixture comprising Phi6 reaction buffer, 0.005 µM of the purified RNA templates, 1.5 mM MnCl2, 0.025 u/µl Phi6 RNA-dependent RNA polymerase (Fisher Scientific (Finnzymes), Pittsburgh, Pa.), 0.2 mM ATP, 0.6 mM rGTP, 0.2 mM CTP, 0.2 mM UTP, 0.2 u/ml SUPERase-In™ RNase inhibitor (Ambion/Life Technologies, Foster City, Calif.), and 20 µM of an invading LNA oligo having the structure shown in FIG. 3B. The mixture was incubated at 40° C. for four hours. After the incubation, 2 µl of 0.5 M EDTA was added to the reaction, and the amplified RNA was purified using the RNeasy® Mini Kit (cat. #74104; Qiagen, Venlo, Netherlands).

It is important to note that the 40° C. incubation was intended to ease the separation of the RNA strands to allow annealing of the invading oligonucleotide, but given the highly stable nature of RNA:RNA duplexes, it was not known whether this temperature would be sufficient until after the experiments were carried out and the results analyzed. Even if it was sufficient, another big unknown was whether the Phi6 polymerase would even function at this elevated temperature, given that its optimal reaction temperature is only 32° C. As such, the results of these experiments were somewhat surprising, and very encouraging, showing that both the 40° C. incubation destabilized the dsRNA enough to allow oligo invasion, and that the Phi6 polymerase could operate well under these suboptimal conditions.

Optimization of RNA Elution Using BluePippin™ Platform

Optimal conditions for use of the BluePippin™ platform (from Sage Science, Beverly, Mass.) to isolate specific sizes of RNA molecules were determined empirically as follows. A commercial RNA size ladder that spans the length of an RNA of interest was purchased from New England BioLabs. Next, the RNA ladder was then run along with a dsDNA ladder on a native agarose gel. The resulting gel image was used to correlate the electrophoretic mobility of dsDNA and ssRNA (i.e., ssRNA of x number of nucleotides in length exhibits the same electrophoretic mobility as dsDNA of y number of base pairs). This correlation was then used to select the appropriate Blue Pippin™ agarose gel concentration and Blue Pippin™ DNA marker. Subsequently, several dilutions of the RNA ladder spanning the expected concentration of the barcoded RNA sample were prepared and loaded in separate wells in the Blue Pippin™ gel. The optimization of the BluePippin™ instrument parameters (e.g., type of the voltage program and collection range), was then performed by starting with a standard BluePippin™ protocol for a given agarose gel concentration and corresponding equivalent in dsDNA length. Following elution using different dilutions of the ladder, the yield was determined using an RT-PCR assay, and the BluePippin™ instrument parameters that provided the best yield of the desired RNA size were chosen for purification of the barcoded RNA sample. For example, exemplary conditions determined for BluePippin™ purification of a 1.8 kb mRNA comprised a 0.75% dye-free agarose gel from Sage Science; a length range set on the BluePippin™ instrument of 1250-2500 bp; use of the low voltage program on the instrument; and the 1-6 kb Marker S1 from Sage Science. Exemplary conditions were also determined for BluePippin™ purification of a 450 nt mRNA that comprised a 2% dye-free agarose gel from Sage Science; a length range set on the BluePippin™ instrument of 400-600 bp; and the Marker M1 from Sage Science.

One-Step RT-PCR Reaction for Synthesis and Amplification of cDNA Molecules

Figure 5:
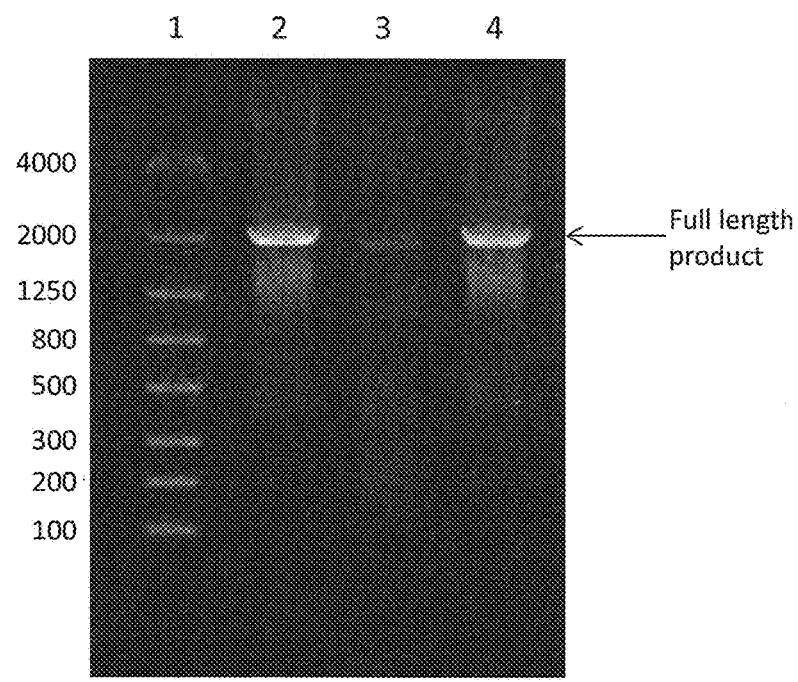
FIG. 5 provides an image of a gel showing the generation of full-length amplicons from this one-step RT-PCR methodology.

The linearly amplified RNA molecules were used to synthesize cDNA, which was amplified, and both the synthesis and amplification reactions occurred in the same reaction volume. The reaction mixture comprised 0.8 mM $MgSO_4$, 20 pg/µl of the amplified RNA, 0.2 µM of primer A, and 1× concentrations of "reaction mix" and "enzyme mix" from the SuperScript® III One-Step RT-PCR System with Platinum® Taq High Fidelity (Life Technologies Corporation; catalog #12574035). The amplified RNA and primer A were pre-mixed and incubated at 65° C. for 5 minutes prior to a fast cool to allow primer A to bind to the RNA amplicons. The remaining components were added at this point. The reaction was then incubated at 60° C. for 30 minutes, and 94° C. for 2 minutes when primer B was added to a final concentration of 0.2 µM. Subsequently, the mixture was subjected to PCR amplification comprising 40 cycles of: denaturation at 94° C. for 30 seconds, annealing at 55° C. for 30 seconds, and extension at 68° C. for 3 minutes. A final extension was carried out at 68° C. for 5 minutes prior to purification of the resulting amplicons on a PCR purification column from Qiagen (Venlo, Netherlands). FIG. 5 provides an image of a gel showing the generation of full-length amplicons from this one-step RT-PCR methodology. Full-length product is produced when the first-strand cDNA primer is present, regardless of the presence of the second-strand cDNA primer.

Temperature Cycling with Long Templates

Figure 6:
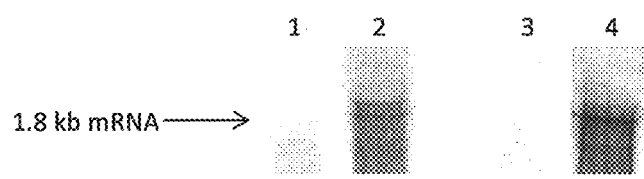
FIG. 6 provides an image of a gel showing the results from an amplification reaction using temperature cycling.

A 1.8 kb mRNA molecule was subjected to a linear RNA amplification reaction during which the temperature was cycled between an optimal temperature for the Phi6 replicase (e.g., 32° C.) and an optimal temperature for the strand invasion (e.g., 40° C.). The time allowed for strand invasion was one minute per cycle, and the time for nascent strand extension was either six minutes or 22 minutes. A higher fold-amplification was observed in the reaction having the longer nascent strand extension times, as shown in the gel in FIG. 6.

Linear Poly-Acrylamide as Carrier Polymer

Figure 7:
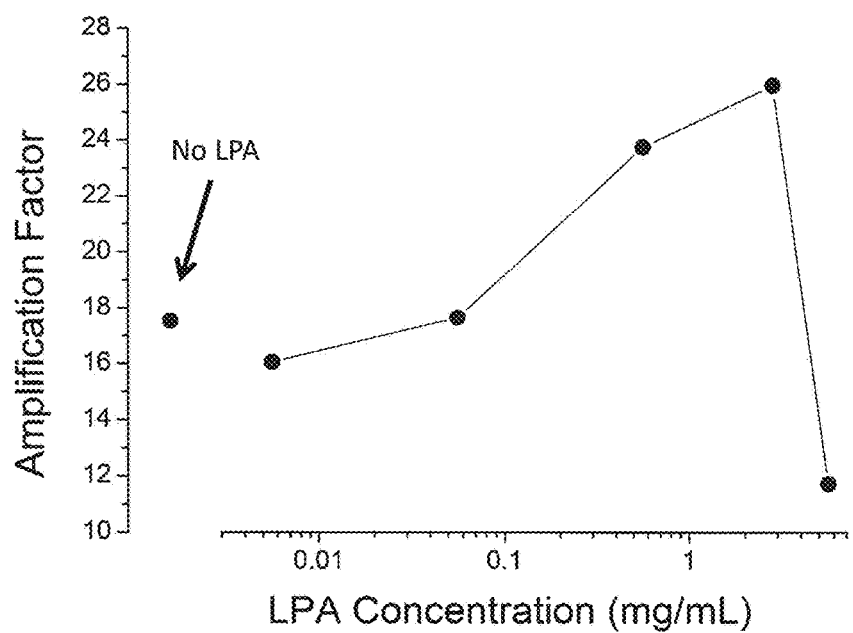
FIG. 7 provides an image of a gel showing the results from an amplification reaction using linear poly-acrylamide as a carrier polymer.

Carrier polymer can be used as an additive in the preparation of low-input amount RNA samples during all the purification steps. Carrier RNA is most commonly used for this purpose, but we have demonstrated that the presence of carrier RNA decreases the efficiency of RNA amplification (data not shown). Linear poly-acrylamide (LPA) were used as an alternative carrier polymer in purification protocols for low-input RNA samples. The increasing concentrations of LPA were tested in RNA amplification reactions to test its feasibility as a carrier polymer in this application. The test was carried out with 0.5 kb mRNA using the temperature cycling program (i.e., 40 cycles of 6 min @ 32° C. and 1 min @ 40° C.). The results are shown in the graph shown in FIG. 7. These data demonstrated that LPA seemed to have no inhibitory effect on RNA amplification up to 2.8 mg/mL; in fact, it appeared to stimulate the amplification reaction when present at a concentration between 0.56 and 2.8 mg/mL.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of performing a linear amplification of a plurality of RNA molecules, the method comprising:
  a) providing a sample comprising a plurality of RNA molecules, wherein the plurality of RNA molecules comprises RNA molecules having differing nucleotide compositions and wherein each of the plurality of RNA molecules comprises a 3' end;
  b) linking an adaptor to the 3' end of each of said plurality of RNA molecules, wherein each adaptor comprises a barcode sequence and a Phi6 RNA replicase initiation sequence, wherein the barcode sequence is positioned 5' to the Phi6 RNA replicase initiation sequence, and further wherein each adaptor has a different barcode sequence;
  c) synthesizing a complementary nascent RNA strand for each of the plurality of adaptor-linked RNA molecules by contacting the plurality of adaptor-linked RNA molecules with a Phi6 RNA replicase, thereby generating double-stranded RNA molecules;
  d) providing an oligonucleotide complementary to a segment of the first nascent RNA strand of each of the double-stranded RNA molecules, wherein the segment is complementary to at least a portion of the adaptor;
  e) annealing the oligonucleotide to the first nascent RNA strand of each of the double-stranded RNA molecules, thereby separating the 5' end of each of the first nascent RNA strands from the 3' end of each of the plurality of adaptor-linked RNA molecules;
  f) repeating said synthesizing, whereby the first nascent RNA strand is displaced and a second nascent RNA strand is synthesized; and
  g) repeating said annealing and said synthesizing multiple times, thereby performing linear amplification of the plurality of adaptor-linked RNA molecules and producing a pool of amplified RNA molecules.

2. The method of claim 1, wherein said multiple times is at least ten times.

3. The method of claim 1, wherein the oligonucleotide is an LNA oligonucleotide.

4. The method of claim 1, wherein the oligonucleotide is 5'-adenylated.

5. The method of claim 1, wherein the adaptor is dideoxy-modified on the 3' end.

6. The method of claim 1, wherein the barcode sequence comprises randomized bases.

7. The method of claim 1, further comprising converting the pool of amplified RNA molecules to cDNA.

8. The method of claim 1, further comprising determining nucleotide sequences for the pool of amplified RNA molecules, wherein the nucleotide sequences comprise sequences that descended from the plurality of RNA molecules and barcode sequences.

9. The method of claim 8, further comprising using the barcode sequences to link each of the nucleotide sequences to a single parental adaptor-linked RNA molecule.

10. The method of claim 1, wherein the annealing is carried out at 40° C. and the synthesizing is carried out at 32° C.

11. The method of claim 1, wherein the annealing and synthesizing are carried out at a single temperature that is at least five degrees higher than an optimal temperature for the Phi6 RNA replicase.

12. The method of claim 11, wherein the temperature is 39-41° C.

13. A method of performing multiplex analysis of retroviral populations, the method comprising:
  a) providing a sample comprising a plurality of linear RNAs from a retroviral population, wherein the retroviral population comprises multiple viral genomes having a different set of sequence variants, and wherein each linear RNA comprises a 3' end;
  b) linking an adaptor to the 3' end of each of said linear RNA, wherein the adaptor comprises a barcode sequence and a Phi6 RNA replicase initiation sequence, wherein the barcode sequence is positioned 5' to the Phi6 RNA replicase initiation sequence, and further wherein each adaptor has a different barcode sequence, thereby generating adaptor-linked viral RNAs;
  c) synthesizing first nascent RNA strands for each of the adaptor-linked viral RNAs by contacting said adaptor-linked viral RNAs with a Phi6 RNA replicase, thereby generating double-stranded RNA molecules;
  d) providing an oligonucleotide complementary to a segment of the first nascent RNA strands of each of the double-stranded RNA molecules, wherein the segments are complementary to at least a portion of the adaptor;
  e) annealing the oligonucleotide to the first nascent RNA strands of each of the double-stranded RNA molecules, thereby separating the 5' ends of the first nascent RNA strands from the 3' ends of the adaptor-linked viral RNAs;

f) repeating said synthesizing, whereby the first nascent RNA strands are displaced and second nascent RNA strands are synthesized;

g) repeating said annealing and said synthesizing multiple times, thereby performing linear amplification of the adaptor-linked viral RNAs and producing multiple nascent RNA strands complementary to each of the adaptor-linked viral RNAs;

h) converting the multiple nascent RNA strands complementary to the adaptor-linked viral RNAs into cDNAs, thereby generating a pool of cDNAs in which all members of the pool of cDNAs that are descended from the same adaptor-linked viral RNA comprise identical barcode regions;

i) determining nucleotide sequences for the members of the pool of cDNAs, wherein the nucleotide sequences comprise adaptor-linked viral RNA sequences and barcode sequences;

j) grouping the nucleotide sequences based on the barcode sequences, wherein all nucleotide sequences from members of the pool of cDNAs that are descended from the same adaptor-linked viral RNA are grouped together, thereby composing one group of nucleotide sequences for each of the adaptor-linked viral RNAs; and k) using the adaptor-linked viral RNA sequences in each group composed in j) to construct a consensus sequence for each of the adaptor-linked viral RNAs.

14. The method of claim 13, wherein the plurality of linear RNAs comprises fragmented viral genomes.

15. The method of claim 13, wherein the plurality of linear RNAs comprises full-length viral genomes.

16. The method of claim 13, further comprising amplifying the pool of cDNAs prior to determining their nucleotide sequences.

17. The method of claim 13, wherein the synthesizing the nascent RNA strands is imperfect such that some of the nascent RNA strands comprise errors, and further wherein the consensus sequences do not comprise the errors in the nascent RNA strands, but do comprise the sequence variants present in the adaptor-linked viral RNAs from which the cDNAs descended.

18. The method of claim 13, wherein the converting the multiple nascent RNA strands complementary to the adaptor-linked viral RNAs into cDNAs is imperfect such that some of the cDNAs comprise errors, and further wherein the consensus sequences do not comprise the errors in the cDNAs, but do comprise the sequence variants present in the adaptor-linked viral RNAs from which the cDNAs descended.

19. The method of claim 13, wherein the oligonucleotides are LNA oligonucleotides.

20. The method of claim 13, wherein the oligonucleotides are 5'-adenylated.

21. The method of claim 13, wherein the adaptor is dideoxy-modified on the 3' end.

22. The method of claim 13, wherein the barcode sequence comprises randomized bases.

23. The method of claim 1, wherein the Phi6 RNA replicase initiation sequence is 5'-UUUUUUUCC-3'.

24. The method of claim 23, wherein the oligonucleotide comprises a 3' sequence selected from: a TTTTTTTCC-3' DNA sequence and a UUUUUUUCC-3' RNA sequence.

25. The method of claim 9, further comprising grouping the nucleotide sequences that descended from the same parental adaptor-linked RNA molecule into sets based on the barcode sequences and constructing a consensus sequence for the parental adaptor-linked RNA molecule for each set.

26. The method of claim 13, wherein the Phi6 RNA replicase initiation sequence is 5'-UUUUUUUCC-3'.

27. The method of claim 26, wherein the oligonucleotide comprises a 3' sequence selected from: a TTTTTTTCC-3' DNA sequence and a UUUUUUUCC-3' RNA sequence.

\* \* \* \* \*